(12) United States Patent
Roitsch et al.

(10) Patent No.: US 7,012,173 B1
(45) Date of Patent: Mar. 14, 2006

(54) PROMOTER SYSTEM AND PRODUCTION AND USE OF THE SAME

(75) Inventors: Thomas Roitsch, Wurzburg (DE); Marc Goetz, Netherby (AU)

(73) Assignee: Freistaat Bayern, (DE)

( * ) Notice: Subject to any disclaimer, the term of this patent is extended or adjusted under 35 U.S.C. 154(b) by 436 days.

(21) Appl. No.: 10/009,966

(22) PCT Filed: Jun. 13, 2000

(86) PCT No.: PCT/DE00/01944

§ 371 (c)(1),
(2), (4) Date: Dec. 12, 2001

(87) PCT Pub. No.: WO00/77187

PCT Pub. Date: Dec. 21, 2000

(30) Foreign Application Priority Data

| Jun. 12, 1999 | (DE) | 299 09 998 U |
| Apr. 4, 2000 | (DE) | 200 05 992 U |
| Apr. 26, 2000 | (DE) | 200 07 494 U |

(51) Int. Cl.
*C12N 15/29* (2006.01)
*C12N 15/82* (2006.01)
*A01H 5/00* (2006.01)
*A01H 5/08* (2006.01)
*A01H 5/10* (2006.01)

(52) U.S. Cl. ............... 800/287; 800/271; 800/274; 800/278; 800/303; 800/320.1; 536/23.6; 536/24.1; 435/201; 435/320.1; 435/419; 435/468

(58) Field of Classification Search ............... 800/278, 800/287, 271, 274, 303, 320.1; 536/23.6, 536/24.1; 435/201, 320.1, 419, 468
See application file for complete search history.

(56) References Cited

FOREIGN PATENT DOCUMENTS

| WO | WO 98/41643 | * | 9/1998 |
| WO | WO 98/59061 | * | 12/1998 |

OTHER PUBLICATIONS

Greiner et al. Plant Physiology 116: 733-743 (1996).*
Roitsch et al. Plant Physiology 108: 285-294 (1995).*
Mariani et al. Nature 347: 737-741 (Oct. 1990).*

* cited by examiner

*Primary Examiner*—David T. Fox
(74) *Attorney, Agent, or Firm*—Pendorf & Cutliff

(57) ABSTRACT

The present invention relates to nucleic acids coding for promoters, which are both tapetum-specific and pollen-specific, as well as the use thereof for producing male sterile plants.

21 Claims, 22 Drawing Sheets

Fig. 1A
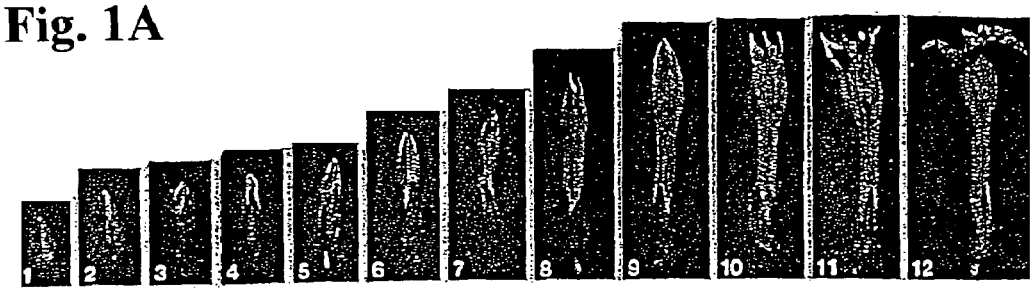
Fig. 1B
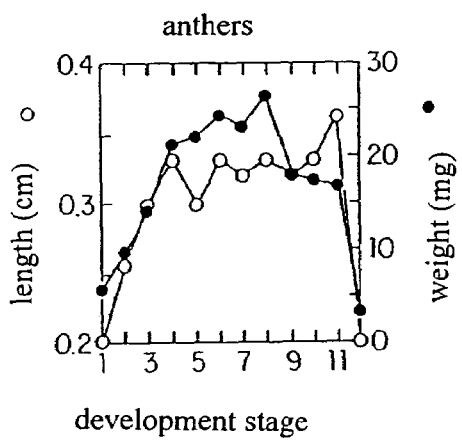
Fig. 1C   Invertase activity in tobacco pollen
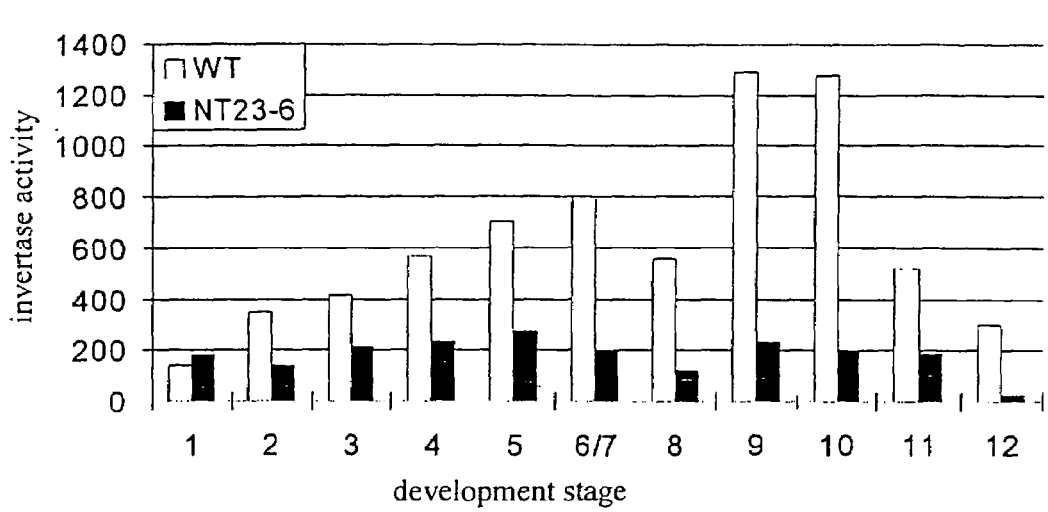

Fig. 5A

Promoter DNA sequence of the extracellular invertase NIN88 from tobacco

```
   1  TCTAGAATGA CGCCACCGGC CAGGACGGGG AGTATGATTT CCCCGAATGT
  51  TCGTTCAACT GCATTGTTAA AACCTGTTAG CGTGATGCAG CCCGGTACTA
 101  TCTTATCCTC GAGTTTCATT TGTGCAAGTA CTCGAGGATG GACAATTCAC
 151  GGGCCACTCC CATCGTCCAC CATAATGCGT CTTACATCTG TATCTAATAT
 201  TCGTAAAGTG ATAACGAGGG CATCATAGTG AGGGAAAACC AAACCGTGGT
 251  TATCTGACTT ATCGAAGATG ATACTTTCTT TAAGTTTCTC GTACCGTTCA
 301  TGAGTGATTA ACTGTTTGAG CTTGTGGGTT GTGGCGAACT TTACGTTGTT
 351  GATCGAAACG TCGTCTCCGC CCCCGATGAT AATGTGAATG GTGCGAGTCG
 401  GTAAGGGTGG TTTCGGCGGT CCCTGGTGTT GTTCACGTCC TCGAGAAAAG
 451  TTGGTCCTTC CTCGGTCACA CAACAATATT TTGAGGTGTC CTTGATGAAG
 501  CATGTCCATG ACCTCTTGTC TTAGGGCGAT ACAATCCTCA GTTTTGTGAC
 551  CTCGCTCTTG GTGGAACTCG CAGAGGGCAT CTGATTTTCT AGTGCTTGGA
 601  TCTGACCTCA TCTTTTGTGG CCACTTTACT TTTGGTCCGA GCTTCTTCAA
 651  TGCATAGACT ATTTCTGAGG GTGACACACA AAATTTGTGA GCGGATAGTA
 701  AAGAGGGCAT ACCTCTCTCG TTCCGGTGAG TCCCTGTCCT TGGCCTAGAT
 751  GGGCCCTCTT CGTAGCGGGA GAGGGGCATG ATGGCACTTT TGACATATCG
 801  TTGATCCATT TCTCGGTTAG ATCATGGAGC TGCAAGATCT CTCTTGGCAT
 851  CATTTTGACG ATCCTTCCTG GTTTCGGCTT GTACCGAGGT CAATCGATGA
 901  GTTGGCCCAT TCAGGTCGTC TTCGTCGGCA CGGGCCTCAG CACAGTAGGC
 951  GTTGTGTATT TCATCCCAAG TGGTTGGAGG ATATTTCATA AGTTGGTTTA
1001  ACAGTTTTCT GGTCGCCCTC GAGCCATTCA TGTTCAGCCC ATTCTGGAAA
1051  GTTGCTACAA CCATTCCTTC TGATACATTC GGTAAGGTCA TCCTTACTCT
1101  GTTGAATCGA GCGAGGAAGT CCCTCAATCC CTCTCCGAGT GATTGTTTGA
1151  TGGCAAATAT ATCGTTCACT CTTGCCTCCG CGTTTTAGC CCCAACATGG
1201  GCCATTATGA ACTTGTCGGC CATCTCTTCG AATATTTCAA TGGAGCGCGC
1251  GGGCAGCTGT GAATACCAAG TCAATGCTCC TCCGGTAAGG GTCTCGCCGA
1301  ACATTTTCAA CAAGATGGAG GAGACTTGTT CTTTGGAGAG ATCATTGCCC
1351  TTTACCGCAG TGACATAATG ATTACATGAT CTTCGGGGTC GGTCGTACCA
1401  TCATAAATTT TCAGATAAGG TGGCATCTTG AACGTCTTGG GTATGGCATA
1451  TGGGGCGGCT TCATCACTGT AGGGTTGCTC GACTAACCGA CCAGCGTCTC
1501  TTTTTGGAAA TATTTTTGGG GCACCCGGTA TTTTATCGAC TCTTTCTTGG
1551  TGTTCTCTCA TTTGATCCCG AAGCATTTTA TTTTCGTTTT CCATTTCTTC
1601  CATTTTCTTC AGAATGGCCG TGAGGGTGTC ATTACCTGCA TTATTAATAT
1651  TGTGAGTGAT ACCTGTTACT GAAGGGGGAG GGTCGTGCTG TTTGGTCATT
1701  GCTGGTGCAA TGCAAGTCCT TGCATTTTCT CTAAATACCT CCTGAGTGGG
1751  TTTGTTGAGG ATGCCGGTCA GCATATTTGT CAGCCAAGCT TCGAGTAGCT
1801  TCTTCACCGC TGGTGGCGCC TCTTCCGTTG TGGACGTGGA AGCTCCTTTA
1851  CCGCGGGATG TTGCGATACT GCTGTGAGGG AGGGGTGATC CACTTCGTCG
1901  GGGAGAGGTG TTAGGCGTTA TGCCTTCGCC TTCTATTTCG GAGACCTCAT
1951  TGATGGTGTT TAAGAGGTTG GTAGTGAGAT TGGCCACTGC CTTCATCCTT
2001  TCTTCTCCCT TACCTGCCAT GTCAGATCTG GGTGTACAAG GAAGTAGGAG
2051  CTTCTCTTCT TCTTTTTTGT GAATTGTGCC AGTTATAGAT CTAAAAGAAA
2101  CTAAAGTTTT AACTAGACTA TCCTCACAGA CGGCGCCAAA TTGTTTGACC
2151  AAAAAATATA GACTTTTGAT TAAATTAATT AATATTGTAT GACAAAGGAT
2201  TAAACCTAGT TAATGATAAT AACTTCAGAT CTATAATCAA TTAACAGCAA
2251  TCACGGTCAT AGCAGCGTTG AGAGAAGATT AAATGTGATG TYCATTCAAT
2301  ATTTCAAGAT CATTAATGAT AGGGGAATAT CAAGCAATAA ATAACGATAA
2351  ATGGCATTAA AGTAAATAAG GAGAATGATT CACCCAATAT TGAATGAGGT
2401  GGATGATTCT TCTTTTTGAC AATGATGAAT GATGGGCAAA TACTAGAATG
2451  TTGGGACCCT TCTCGGATCT AATGAAAAAA GTATGGAATA GTAGATAATC
2501  GAATCTCTTT AGAAAGGTAG TGATTGTCTT TTATCTAGAG AGAAAGTCTG
2551  CTTTTCAAAG AATATTTTA TCAGAGAATA TTACATCCCC CTCTCTCCCT
2601  ATCTCTTTTT CTATTTATAT GGGACATTCC TCAATCAATC CTAAAAGTAC
2651  ATACACCAAG AATATTCAAT AAAATATTTT TTGAATATT CTATTATAAA
2701  AACTAGCTGT TAGCACTCGA CCTCGGTCGY TATTGACTAC TCGGTTACGA
2751  GCCCTGTCAT TTACTAATCG ACCTCGATTA CATCACTTTC TACGATACTG
2801  CTTCATGTCA AATCTTAATG AAAGCAGATT TTGACCCATA CAATAATATG
2851  ACAAAATTGC TTCCAAAGAA AACATGGCTC TTATAGTGAA ATATCGTTAG
2901  ACTGTTATAG AAAGATCTGA ATTTATTTAT AAGAATAGTG TTTTTTTCTT
2951  TTCTTTTCAT ATCTAAGGAG TAAAGCAACC ATGAATAGAA AAGGCTTAGT
3001  AACTATATAT CAAAGGAATG GTGTTTTTTC TTTAAATATG GATAAAAATT
```

Fig. 5B

```
3051  TGTGAATATA GAAGATTAGA TCAATTAACA AAGGTTATGG TGGAGTGGTA
3101  AGCAGAGGCG GACCTATGTG TTATAGTAAG GGGTCACCCA CTACTAGAAA
3151  TCCGGTAAAG ATCGATCAAA AAACCGACCA ACATTGGTCG GTAATGGCCA
3201  AAAACTGACC AAAACGCGAT CATTTACGTG TGAACGGTAT TTTTATGGTC
3251  GGAAAGGAAT ACCGACCAAA GTTGGTCGGA AATTACCGAC CAACTTTGGT
3301  CGGTCAATTA AATTCAAAAA AAATATTGTA AAAAAAAACC GACCAAAGTT
3351  GATCGGTATT TTAATTATGT AATAAAAAGA TTCACTATCT GGGAATCGAA
3401  CCGGGGTCTG TACTATGGCA AGATACTATT CTACCACTAG ACCATTGGTT
3451  CATTTTGTTT TAAGACTGTC TTTTATTTGA TTTATACTCT TTAATTATAT
3501  TTTTGCACGA AAATAACCGA CCAAAGTTGG TCGATTTTAT TAAAAAGTAA
3551  AATTACTTAC CAAAGTTGGT CGATTTTTTT AAATGATCCG CCGAATTAAC
3601  CGACCAATTT TGGTAGGTTT TTTTAATATT AATTTTTATT TATTTTAATT
3651  GAAAAACTAA CCAAAGTTAG TCGGTTTCTT GAAACATAAA TTTCGCGGGA
3701  CTCAAAAATA GTTTCCCGCA TTTTTGCGCC AAAGAAAACC GACCAAAGTT
3751  GGTCGGTTTC GTAAAAAAAA AAAAATTTA AAAATATAT TTTAAAAAAC
3801  CGACCAACTT TAGTCGGTTT TTTGGTCGAT TTTTTGACCG ACCAAAGTTG
3851  GTCGGTCGAC CTTGGTCGGT TTTTGCCGAA TTTCTAGTAG TGACCGAACC
3901  CTGTAAGCTT CGGGAGAAAT TTTGTATATG TATATGTGTA TATCCTTAAA
3951  ATGATTAATT TAAAGAACGT GGCACCCTGA ATACTAGAAG CCTTTAGGGG
4001  CACTAGATGA GCAGAATAAC GTGTTCTCGT CGCGTAAAAA TACTTGGATC
4051  CGCCTATGAT GGTAAGTACT TCTTCGTCCT TAATCAGAGG TTTCGACTTC
4101  GAGCTCCAGA TATAAACTAT AGACTCGTCT TTATAGCACC TTTTAATAAG
4151  ACTATGACTT CATCTGATTT CTCTATAAAT ACTCCTCAAG CTTTCGGTTC
4201  TTCTCCATTG TTCAGTTTCT TTCTCCACAT CACAGAAGTG AAAACAAAAC
4251  AAGAAGAAGA AGAAGAAGAA AAATAAAGAG TTTCTGTCAA ATTAAGTCCA
4301  ATAGGGAAAA TG
```

Expression of NIN88-promotor
GUS fusion in transgenic tobaccoplants
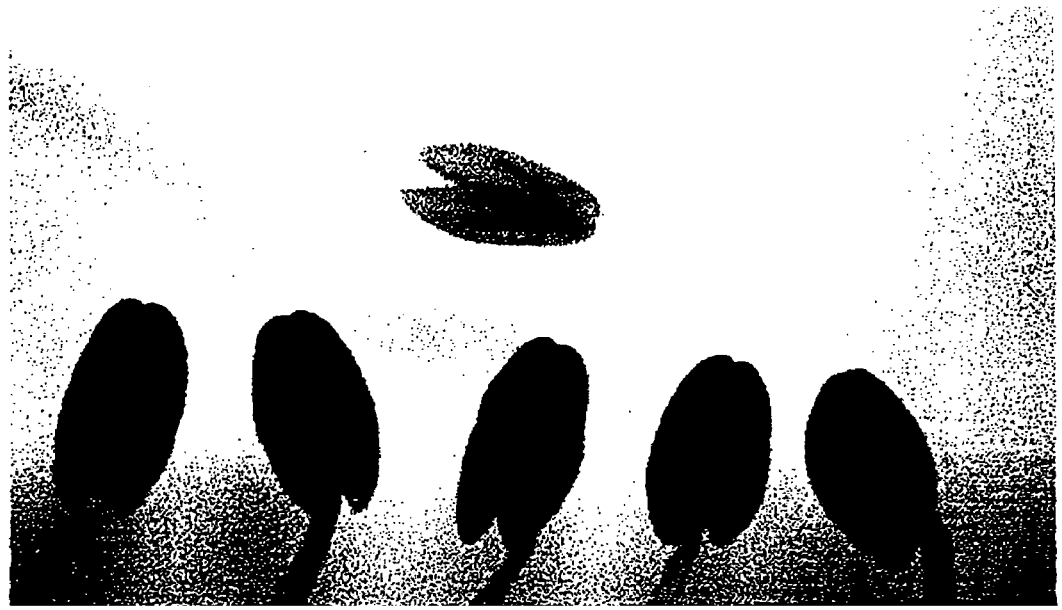
Fig. 6A
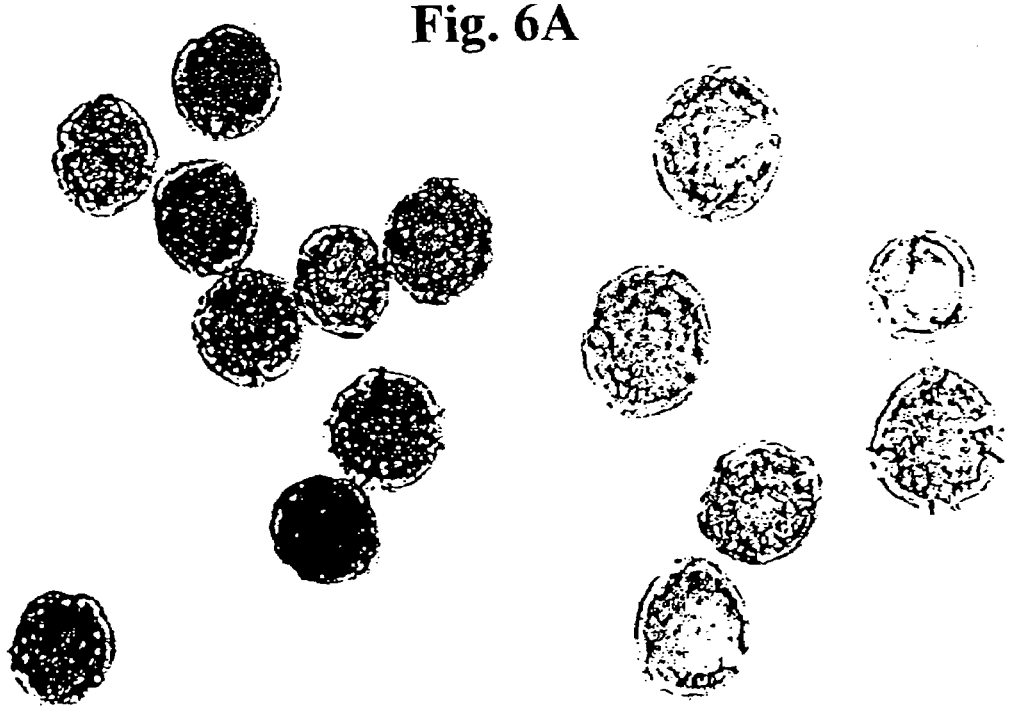
Fig. 6B                    Fig. 6C

Fig. 7
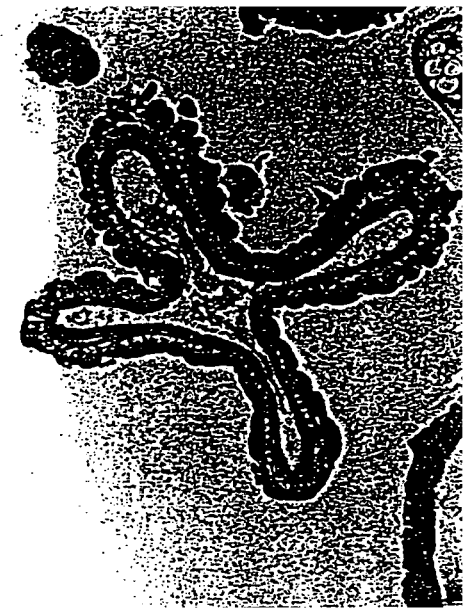
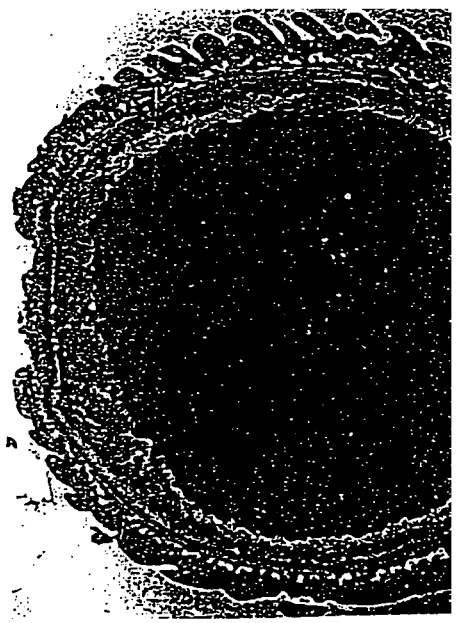
wt — NT23-81
REM (2700x)
TEM (5500x)

Fig. 10
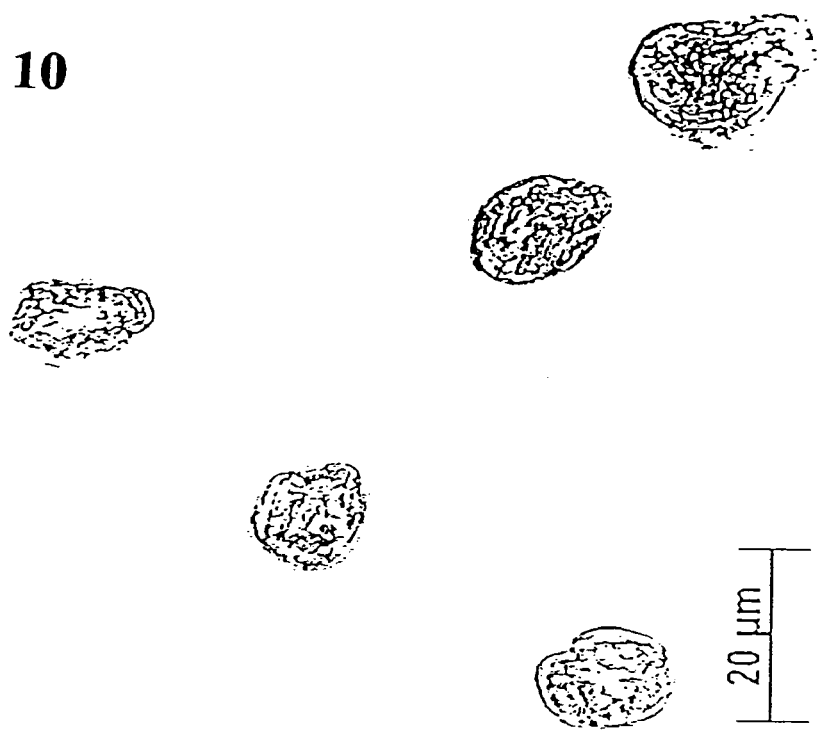
NT23-6
20 μm
wt
20 μm

Fig. 12
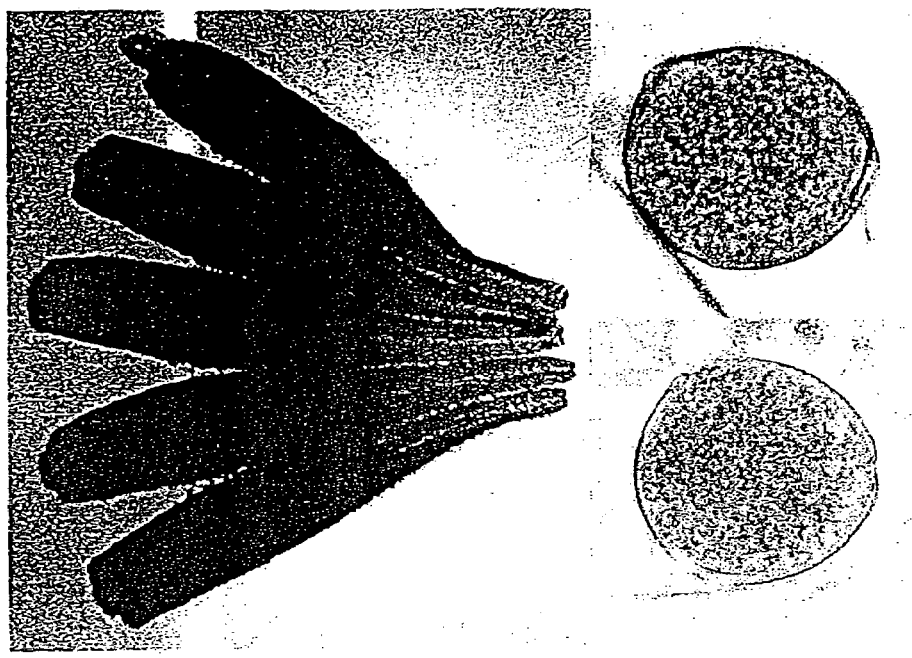
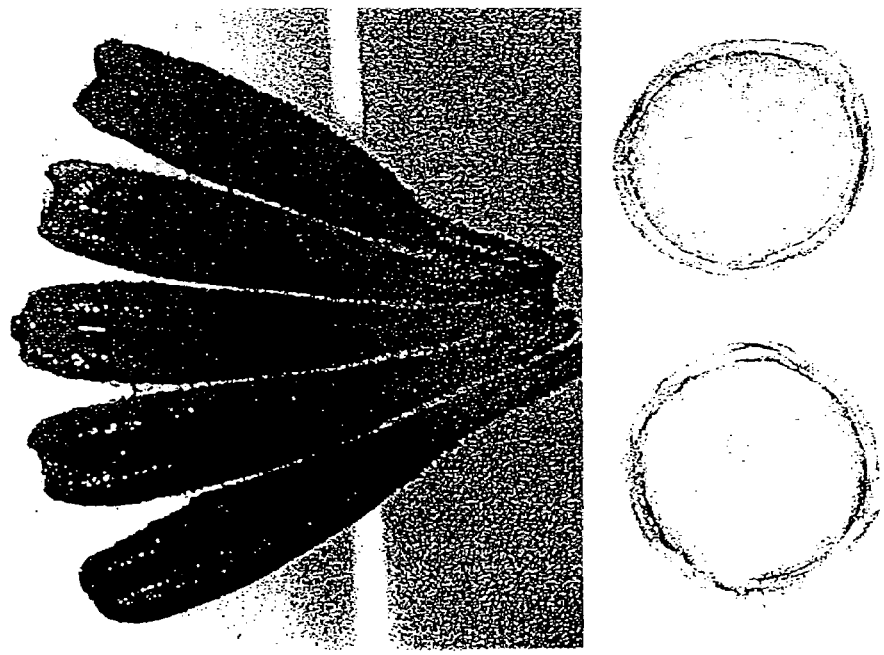

Fig. 15A

Genomic sequence of NIN88

```
   1  ATGGAGCTGT TTAGAAAAG  CTCTTTTCAT TGTGCTTTGC CAGTTTTCAT
  51  ATTATTGGTT TGCTTGTTTA TAATTTTATC TAACTATGTT GTGTTTGCTT
 101  TCAATTATGA CGTTTTTACG TGCTTCCAAT CCTCAAAAGA TGCTAATATC
 151  ACTTCTAACT ACAGAACTGG TTACCATTTT CAACCCCCCA AGAACTGTAT
 201  GAATGGTACG TTTCTCTCCC CTTCCACCCA CCCCACCCCC TCTTCTGTTG
 251  TTGCTTTTGA TATGTGTATA TATATATATA TATCCATTTT TTGCTCGGTA
 301  TCGGCATTAG GATCCACTAA ATTCGGCATT GAGGGGTAAT TAGGCGTCTA
 351  ACAAAGTCAA TTCCATAACT AGGGCTCGAA CCCGAGACTT CCGATTAAAA
 401  ATGAAGGAGT ACTTAACACT TATTCTGTAA CATTAAACAA TAGACATCCT
 451  ACTCCTCTAA ACTCATTTGT ATTTTTAAAA TATCTATTTT ACCCTCGATC
 501  TTATTAGCCT TCATCTACTT TTTTTTTTTT TACTTTTTTA ATATCACAAT
 551  ATTTTCTTAT TCTATGTTAT GAATTTACCT ATAGTGAACA TAAAATTTAA
 601  AAAAGGTGAA AAACAATAAT CAATCATATA CTTATTGAAG TTAGAATAAT
 651  GAAACAAATG GGCGCAATTA AAATATTAGA ATAACAGATC TTATTAATAT
 701  CAATCAAATA AAATTTAGTT CAGTAATATA AAAAAATAAT TAAACATAGA
 751  GGTAGATTTT CTAAGAAATT CCTAAAAGAT TATATATTTA TAACTTAGAA
 801  AATATTTTGT TAATGAAAAT AAATATTCAA AGATATATAC AGAACAACAA
 851  CAACAACCCG ACCTTACCCC TACCCTGGGG TAGAGAGACT GTTTCCGATA
 901  GACCCTCGGC TCCCTCCCTC CAAGAACTCC CCACCTTGCC CTTGGGATGA
 951  CTCGAACTCA CAACCTCTTA GTTGGAAGTG GATGGTGCTT ACCACTAGAG
1001  CAACCCGCTC TTGTCCGAAG ATATATACAG AAACATGTAA TAAAGAATAA
1051  AAGAGAAAGT AAAACTTAAA TATATAGATA ATATTAATGT AACGATAAAA
1101  AAGAGTAACG ATAATTGTTT TTGCAAATTC ATAAAGGTAT TATTCTAGTT
1151  AAATTTTATT GAGTTTTAAT TATATAATTT ATCATAAGAT ATTAAAATTG
1201  GTAAAATACT TAGGCTAATG ATAAAATACA TCTTATATAA TATTAAAAAA
1251  AATAGAGGAG AAATTGAAAA TGTCAAGGGT AAAATAGAAA ATGCATATGA
1301  TAGGAGGAGC GAAATATATA TTATTTAGTG TTGGAAGAGT GATTTGATTT
1351  TTAAGATAAA ATTAGGGGAT GAAAATGATT TTTACACTTT AATAGATAGA
1401  TCCTACTGAA ACACGTGTGA GTTCCAAAAG CAAAAAACGA AAAAGGAACC
1451  AGCTCCCTAA TAATGAGTAC TTATTATACA AGTAAATACA ATTAGAGGAC
1501  ACTAATTGCA ACCCCCTACT TGGGAACTGT CGGCCTATTG CTTTAATTAC
1551  TTATACTCTC ACTCCGTTCA CTTTTACTTA TCCAATATTC TAAGTGACAT
1601  TTGGACATAA GAATTGTAAA ATTCCAAAAT AGGAAAAAAA AATACAAGTG
1651  AAAATGTTAT TTGAAATTTA GAGTTACGTT TGGACATGAA TATAATTTTG
1701  GGTTGTTTTT AAAGTTTTGT GAGTGATTTG AGTGAAAATT TTGAAAAACA
1751  GTTTTTTGAA GTTTTTCAAA TTTTCGAAAA TTTTCAAAAT GCATCTTCAA
1801  ATGAAAATTG AAAATTTTAT GAACAAACGC TGATTTCGAA AAAAAAGTGA
1851  TTTTTTTGTG GAAAAAAGAA AAAAATTTCT TATGTCCAAA CGGGCTCTAA
1901  AAATAGATTT TCACTTTTAC TTGTCACTTT TCGCATATCA AGAGAAGACA
1951  ATTTCTTTTT TTCTGTTATA CTCATAGTAT TAATTACTCA TTTCAAATCA
```

Fig. 15B

```
2001  TTTTTTCAAA TCCACTAAAA ATATGTATCA ATTAATATGG GTATTATGGT
2051  AAATTATGCA CTTCATTTAT TATTTCTTAA GGAGTGTTCA AAGTCCGTAG
2101  TAGACAAGTA AAAGTGAATG GAGAGAGTAA TAAATTACAC CTACTTTCTT
2151  GGAAATACCA GTTGAGACAT ACGTAGAACT TTTGCTAATT TTTTCTTATT
2201  TTTTCTTAAT TATATTATAT TTGTGTGTGA TATGGGCAGA AGGGGTTGGT
2251  AAGAAGGATC TTGTCCCCAT CAGCAACTTA CAATATTTTA GGGAAGACAA
2301  ATAATAATTT TCTGCATTTC CTAAATTTTT GTAATTTCAC TTTTCATTTG
2351  TTTATTATTT GATTATTCAT CAATATTAAA TTATGCAGAT TTAGTACTCA
2401  CATTCAATTG TTTATTTACA ATTTTTTTA ATTTTTTTCT TTATGGTCTT
2451  TCTCGATGCC TTCAAACATA CAAATAGACC CCAATGGTGA GTCAGAAATT
2501  TTATCTTCTT TTTATATATA TAATTTAATC ACCAATTATT CATTTATGAT
2551  ACTGATTTTT CATGTAATTA CCAACAGCAC CAATGTATTA CAATGGAGTC
2601  TATCATCTAT TCTACCAGTA CAATCAAAAA GGATCAACAA TGAACAACAT
2651  TGTTTGGGCT CATTCAGTCT CAAAAGACTT AATCAATTGG ATTAATTTAG
2701  AGCCTGCAAT TTATCCATCC AAACCATTTG ACAAATATGG AACATGGTCT
2751  GGTTCAGCAA CTATTCTCCC TGGTAACAAG CCCATTATTT TGTACACTGG
2801  AGTGGTAGAT GCCAACATGA CCCAAGTCCA AAATTACGCC GTCCCGGCCA
2851  ACTTATCCGA TCCATATCTC CGTGAATGGA ACAAGCCCGA TAACAACCCG
2901  TTGATCGTCC CGGATATCAG CATCACCAAG ACCCAATTTC GTGACCCGAC
2951  AACAGCTTGG ATGGGCAAAG ATGGTCATTG GAGAATTGTG GTAGGAAGTT
3001  CAAGAAACCG TGGTGGGTTG GCAATATTGT ATAGAAGTAG GAATTTCATG
3051  AAATGGATCA AGGCTGAGCA TCCACTTCAT TCATCTGCCA AAACAGGAAA
3101  TTGGGAATGC CCAGATTTTT TTCCTGTTTC CTTGCAAGGT TCTAATGGTT
3151  TAGATGCATC GTACAACGGA AAATATGTTA AGTACGTTCT CAAGAATAGC
3201  CTTCCTGTTG CCGCGTTTGA GTACTACACA ATTGGTACAT ATGATGCCAA
3251  ACAAGATAGG TATATTCCAG ATAACACTTC AGTCGATGGT TGGAAAGGAT
3301  TGAGACTTGA CTATGGCATT TTCTACGCGT CTAAGTCGTT CTACGACCCT
3351  AGTAAGGACC GAAGAATCGT GTGGGGTTGG TCTTATGAAT TAGATGGTCT
3401  CCCCAATAAT GAAAACAACA AAGGATGGGC CTGGAATTCA GGCTATCCCG
3451  CGTAAAGTAT GGCTTGATTT CAGTGGTAAA CAATTAGTTC AATGGCCTAT
3501  TGAAGAATTA AAAACTCTAA GAAAGCAAAA TGTCCGATTG AGCAACAAAA
3551  GGCTGGATAA TGGAGAAAAG ATTGAAGTTA AAGGAATCAC AGCGTCGCAG
3601  GTTTAGACTT TTTTCTAGTT TTTAATTTGC AAGCATTTTA AATAAAATTT
3651  TCTTCACAAG TTAAGGCTAA GTTGGGACAT CTATTGAAAT TGCCAGGCTG
3701  ATGTTGAAGT GACATTCTCC TTCTCTAGCT TAGACAAGGC AGAGCCATTT
3751  GATCCTAGTT GGGCTGATCT TTATGCACAA GATGTTTGTG CAATTAAGGG
3801  TTCAACTGTT CCAGGTGGGC TTGGGCCATT TGGCCTTGCA ACATTGGCTT
3851  CTCAAAACTT AGAAGAATAC ACACCTGTTT TTTTCAGAGT GTTCAAAGCT
3901  CAGAATTT
```

Fig. 16A

Sequence of NIN88 promotor fused with NIN88 antisense

```
   1  TCGAGCCATT CATGTTCAGC CCATTCTGGA AAGTTGCTAC AACCATTCCT
  51  TCTGATACAT TCGGTAAGGT CATCCTTACT CTGTTGAATC GAGCGAGGAA
 101  GTCCCTCAAT CCCTCTCCGA GTGATTGTTT GATGGCAAAT ATATCGTTCA
 151  CTCTTGCCTC CGCGTTTTTA GCCCCAACAT GGGCCATTAT GAACTTGTCG
 201  GCCATCTCTT CGAATATTTC AATGGAGCGC GCGGGCAGCT GTGAATACCA
 251  AGTCAATGCT CCTCCGGTAA GGGTCTCGCC GAACATTTTC AACAAGATGG
 301  AGGAGACTTG TTCTTTGGAG AGATCATTGC CCTTTACCGC AGTGACATAA
 351  TGATTACATG ATCTTCGGGG TCGGTCGTAC CATCATAAAT TTTCAGATAA
 401  GGTGGCATCT TGAACGTCTT GGGTATGGCA TATGGGCGG CTTCATCACT
 451  GTAGGGTTGC TCGACTAACC GACCAGCGTC TCTTTTTGGA AATATTTTTG
 501  GGGCACCCGG TATTTTATCG ACTCTTTCTT GGTGTTCTCT CATTTGATCC
 551  CGAAGCATTT TATTTTCGTT TTCCATTTCT TCCATTTTCT TCAGAATGGC
 601  CGTGAGGGTG TCATTACCTG CATTATTAAT ATTGTGAGTG ATACCTGTTA
 651  CTGAAGGGGG AGGGTCGTGC TGTTTGGTCA TTGCTGGTGC AATGCAAGTC
 701  CTTGCATTTT CTCTAAATAC CTCCTGAGTG GGTTTGTTGA GGATGCCGGT
 751  CAGCATATTT GTCAGCCAAG CTTCGAGTAG CTTCTTCACC GCTGGTGGCG
 801  CCTCTTCCGT TGTGGACGTG GAAGCTCCTT TACCGCGGGA TGTTGCGATA
 851  CTGCTGTGAG GGAGGGGTGA TCCACTTCGT CGGGGAGAGG TGTTAGGCGT
 901  TATGCCTTCG CCTTCTATTT CGGAGACCTC ATTGATGGTG TTTAAGAGGT
 951  TGGTAGTGAG ATTGGCCACT GCCTTCATCC TTTCTTCTCC CTTACCTGCC
1001  ATGTCAGATC TGGGTGTACA AGGAAGTAGG AGCTTCTCTT CTTCTTTTTT
1051  GTGAATTGTG CCAGTTATAG ATCTAAAAGA AACTAAAGTT TTAACTAGAC
1101  TATCCTCACA GACGGCGCCA AATTGTTTGA CCAAAAAATA TAGACTTTTG
1151  ATTAAATTAA TTAATATTGT ATGACAAAGG ATTAAACCTA GTTAATGATA
1201  ATAACTTCAG ATCTATAATC AATTAACAGC AATCACGGTC ATAGCAGCGT
1251  TGAGAGAAGA TTAAATGTGA TGTnCATTCA ATATTTCAAG ATCATTAATG
1301  ATAGGGGAAT ATCAAGCAAT AAATAACGAT AAATGGCATT AAAGTAAATA
1351  AGGAGAATGA TTCACCCAAT ATTGAATGAG GTGGATGATT CTTCTTTTTG
1401  ACAATGATGA ATGATGGnCA AATACTAGAA TGTTGGGACC CTTCTCGGAT
1451  CTAATGAAAA AAGTATGGAA TAGTAGATAA TCGAATCTCT TTAGAAAGGT
1501  AGTGATTGTC TTTTATCTAG AGAGAAAGTC TGCTTTTCAA AGAATATTTT
1551  TATCAGAGAA TATTACATCC CCCTCTCTCC CTATnTCTTT TTCTATTTAT
1601  ATGGGACATT CCTCAATCAA TCCTAAAAGT ACATACACCA AGAATATTCA
1651  ATAAAATATT TTTTTGAATA TTCTATTATA AAAACTAGCT GTTAGCACTC
1701  GACCTCGGTC GnTATTGACT ACTCGGTTAC GAGCCCTGTC ATTTACTAAT
1751  CGACCTCGAT TACATCACTT TCTACGATAC TGCTTCATGT CAAATCTTAA
1801  TGAAAGCAGA TTTTGACCCA TACAATAATA TGACAAAATT GCTTCCAAAG
1851  AAAACATGGC TCTTATAGTG AAATATCGTT AGACTGTTAT AGAAGATCT
1901  GAATTTATTT ATAAGAATAG TGTTTTTTTC TTTTCTTTTC ATATCTAAGG
1951  AGTAAAGCAA CCATGAATAG AAAAGGCTTA GTAACTATAT ATCAAAGGAA
2001  TGGTGTTTTT TCTTTAAATA TGGATAAAAA TTTGTGAATA TAGAAGATTA
2051  GATCAATTAA CAAAGGTTAT GGTGGAGTGG TAAGCAGAGG CGGACCTATG
```

Fig. 16B

```
2101  TGTTATAGTA AGGGGTCACC CACTACTAGA AATCCGGTAA AGATCGATCA
2151  AAAAACCGAC CAACATTGGT CGGTAATGGC CAAAAACTGA CCAAAACGCG
2201  ATCATTTACG TGTGAACGGT ATTTTTATGG TCGGAAAGGA ATACCGACCA
2251  AAGTTGGTCG GAAATTACCG ACCAACTTTG GTCGGTCAAT TAAATTCAAA
2301  AAAAATATTG TAAAAAAAAA CCGACCAAAG TTGATCGGTA TTTTAATTAT
2351  GTAATAAAAA GATTCACTAT CTGGGAATCG AACCGGGGTC TGTACTATGG
2401  CAAGATACTA TTCTACCACT AGACCATTGG TTCATTTTGT TTTAAGACTG
2451  TCTTTTATTT GATTTATACT CTTTAATTAT ATTTTTGCAC GAAAATAACC
2501  GACCAAAGTT GGTCGATTTT ATTAAAAAGT AAAATTACTT ACCAAAGTTG
2551  GTCGATTTTT TTAAATGATC CGCCGAATTA ACCGACCAAT TTTGGTAGGT
2601  TTTTTTAATA TTAATTTTTA TTTATTTTAA TTGAAAAACT AACCAAAGTT
2651  AGTCGGTTTC TTGAAACATA AATTTCGCGG GACTCAAAAA TAGTTTCCCG
2701  CATTTTTGCG CCAAAGAAAA CCGACCAAAG TTGGTCGGTT TCGTAAAAAA
2751  AAAAAAAATT TAAAAAATAT ATTTTAAAAA ACCGACCAAC TTTAGTCGGT
2801  TTTTTGGTCG ATTTTTTGAC CGACCAAAGT TGGTCGGTCG ACCTTGGTCG
2851  GTTTTTGCCG AATTTCTAGT AGTGACCGAA CCCTGTAAGC TTCGGGAGAA
2901  ATTTTGTATA TGTATATGTG TATATCCTTA AAATGATTAA TTTAAAGAAC
2951  GnnGCACCCT GAATACTAGA AGCCTTTAGG GGCACTAGAT GAGCAGAATA
3001  ACGTGTTCTC GTCGCGTAAA AATACTTGGA TCCGCCTATG ATGGTAAGTA
3051  CTTCTTCGTC CTTAATCAGA GGTTTCGACT TCGAGCTCCA GATATAAACT
3101  ATAGACTCGT CTTTATAGCA CCTTTTAATA AGACTATGAC TTCATCTGAT
3151  TTCTCTATAA ATACTCCTCA AGCTTTCGGT TCTTCTCCAT TGTTCAGTTT
3201  CTTTCTCCAC ATCACAGAAG TGAAAACAAA ACAAGAAGAA GAAGAAGAAG
3251  AAAAATAAAG AGTTTCTGTC AAATTAAGTC AATAGGGAA AATGGAGCTG
3301  TTTGGATCCC CGTTTTCATT ATTGGGGAGA CCATCTAATT CATAAGACCA
3351  ACCCCACACG ATTCTTCGGT CCTTACTAGG GTCGTAGAAC GACTTAGACG
3401  CGTAGAAAAT GCCATAGTCA AGTCTCAATC CTTTCCAACC ATCGACTGAA
3451  GTGTTATCTG GAATATACCT ATCTTGTTTG GCATCATATG TACCAATTGT
3501  GTAGTACTCA AACGCGGCAA CAGGAAGGCT ATTCTTGAGA ACGTACTTAA
3551  CATATTTTCC GTTGTACGAT GCATCTAAAC CATTAGAACC TTGCAAGGAA
3601  ACAGGAAAAA AATCTGGGCA TTCCCAATTT CCTGTTTTGG CAGATGAATG
3651  AAGTGGATGC TCAGCCTTGA TCCATTTCAT GAAATTCCTA CTTCTATACA
3701  ATATTGCCAA CCCACCACGG TTTCTTGAAC TTCCTACCAC AATTCTCCAA
3751  TGACCATCTT TGCCCATCCA AGCTGTTGTC GGGTCACGAA ATTGGGTCTT
3801  GGTGATGCTG ATATCCGGGA CGATCAACGG GTTGTTATCG GCTTGTTCC
3851  ATTCACGGAG ATATGGATCG GATAAGTTGG CCGGGACGGC GTAATTTTGG
3901  ACTTGGGTCA TGTTGGCATC TACCACTCCA GTGTACAAAA TAATGGGCTT
3951  GTTACCAGGG AGAATAGTTG CTGAACCAGA CCATGTTCCA TATTTGTCAA
4001  ATGGTTTGGA TGGATAAATT GCAGGCTCTA AATTAATCCA ATTGATTAAG
4051  TCTTTTGAGA CTGAATGAGC CCAAACAATG TTGTTCATTG TTGATCCTTT
4101  TGGATTGTAC TGGTAGAATA GATGATAGAC TCGAG
```

Fig. 17A

```
   1 CATAATCAAA TGTGTGGTCT TATGTAGAAC TAATATTTGG TAATATTAGG
  51 CAAGTTGTTA TGTGACTTAT TTTATTCAAA AATATAATAA GAAGTTCAAA
 101 GAGAAGAGTA CAAGTAAGTA AGTAAGCAGA GACGAATCCT GGATTTAAAG
 151 GGTCTGGCTA TATTAATGTT TTTTTAATTT AAGCATTAGC GATTCGCCTT
 201 GCAAGTAATC GATAGGACAA AAGTTTTACC TTACTAATTC TATTGAGGCA
 251 CCAAATCCCT ATGAAAAAGC ATGTAAAATA TGAGAAGACG AAAGAATTAA
 301 ATAGGTTATA ATTATTGTAT AATTTATAAC ACACTTTATG ATAATATTAC
 351 AAATAAGAAT ATCGAATATT TAATTAATGA CGAACTATAA AAGCAAAGAA
 401 GGAAGGATGA GCTTCCAAAA ACAATCGCAA ATGAATAAAG ATGCCCAAAA
 451 TAGAGTAACC TAACGAAGTC GATACTTCCA TTCATAATCA AATCTGTTCA
 501 AAAACACTTG ATGGGTTATT TTTAACTTTA AGAGATGTAT CATATCGTCT
 551 CTTATTATTC CTTTAGGGCT ATTCGCCGTA GGAATAAAAT TTATATGATC
 601 AAATTTCACG TTATATAAAT AATGTGAAGA AAAAACTTAT ACTTTTCAAG
 651 GTAACAAGAA ATCATGTTTT TTTTACGCCT TCGTGGAGAC TACTTCCTCG
 701 TAACAAAAAA TTAACATTTT AAGTGGCGAC TCTAAAAACT CGTGGCCAGT
 751 ATATTAGTCG CCATTAAACA TTATTTTTAA TCATGAGTTC TTTTCTTTTT
 801 TAATCTTTTT TTAAGGTCAA ATTTACCACT TTATCTTATT TATTTAAATT
 851 GAAAAATCCC AAATTTTGCA TTATTTTTTT GAATTCCTTT TTTTTTTACA
 901 CACTCAAAAA GTCAAAACAT TAAAAAAACG AAATAGCAAA TTAAATGGCA
 951 AAAGACTTGT TGTAACAAAA AAAAAATAGT AAAACAGACT CATAAAAGGT
1001 AACAATAACC AACAAATCAC ACAAAATTGT AGATAAATAT TATGCAAACA
1051 AATAAAAATT AATAATCCAA TCCATTTATT TATTTTTTA AAAAAAACCT
1101 AAATTAACTC TCCATCTTTC AATCAAAAAC AAACTCTACC CATTTTTTTC
1151 ACTATAAATA CTCTTCATAA TTTTCATTTG TTCTTCATTC CCATGTTTCT
1201 TTTCTCCTTA TCCAAAAAAA AAAAAATTAA AAAAAATTAT TTAGATTAAA
1251 TATCACTATC TGTCAAAGCC CAATCATTAA AATAAAATAA AAATTATGGA
1301 TTATTCATCT AATAAAGTT CTCGTTGGGC TTTGCCAGTT ATCTTAGTTT
1351 GCTTTTTTGT AATTTTATTA TCCAATAATG TTGTTTTTGC TTCTCATAAA
```

Fig. 17B

```
1401  GTTTTTATTC ACTTGCAATC TCAAAATGCC GTAAATGTTC ATACTGTTCA
1451  TCGAACTGGT TATCATTTTC AGCCCGAAAA ACATTGGATC AATGGTATGT
1501  TTATTCCTTT TTTTCGTCTT TTTTTATAT ATATATATAT AATAAAACGA
1551  ACATGTTGTG TTTAGTCTAG ATTTAATACT AGTGATTTTT TTGACGCTAA
1601  CAAATAATCG AGTACTCACC ATTTGTCAAT AGATACATTG ACATGTATTA
1651  GTATGATTTT CGTCTTTTTT CGTTGTTTCT AATATTATTT AATCTTCACT
1701  AATTTTTTA TTTTTCTTTG AATGATGTCT CTTGGTCAAA ACATACAATA
1751  GATCCCAATG GTAAGTTAAC TATATTTTG TATATTTTTT AAATTTATTT
1801  TATTCTTATT ATATAATATA GGGAAAAAAG GATAAATATA TCCCCGAACT
1851  ATTATAAATA GTATGCACCA GTATCCTCTG TTATACTTTA GAGATATTTT
1901  TGCCGTCAAA AAACTAGAAC ACATATATCC TTTATTTATC CCGATATCGA
1951  ATCGATTGTA CCACGAGTGA AGGGTATAGC TCTAGTTTTG GACGGTAGGG
2001  CACCTAAAGT AGACGAAGA
```

PROMOTER SYSTEM AND PRODUCTION AND USE OF THE SAME

This application is a 371 of PCT/DE00/01944 filed 13 Jun. 2000.

The present invention relates in general to gene expression and its regulation in plants. More specifically the present invention relates to a nucleic acid sequence coding for a promoter, expression systems incorporating the same, nucleic acid constructs, vectors, cells, plants, seed obtainable from the plants and processes for the production of male, sterile plants. Even more specifically the invention relates to DNA promoter sequences and expression cassettes, which can be introduced into plants in order to regulate within the same on a time and space basis the transcription of an adjacent, coding sequence.

BACKGROUND OF THE INVENTION

A promoter is a DNA sequence, which influences or determines the expression location and expression quantity of a gene and makes available points for the bonding of RNA polymerase. The position of a promoter is fixed relative to the transcription starting point in the genome of an organism. RNA polymerase is an enzyme, which can connect to the promoter and puts into effect the transcription of a gene, which is under the control of said promoter. This leads to messenger RNA (mRNA), which is in turn used for protein synthesis.

Promoters have been investigated in various organisms. For certain species it was possible to find conserved DNA regions (so-called consensus sequences) within promoters, which are associated with different genes. It is assumed that these regions are bound into the part played by the promoter in the transcription process. The initiation of the transcription process in plants incorporates an interaction of the promoter with the RNA polymerase II. Concensus sequences were found in plant promoters above the 5' end of the transcription starting point. One of these sequences is approximately 7 base pairs long and is approximately 20 to 30 base pairs above the transcription starting point. This sequence is known as a so-called TATA box and it is assumed that it plays a part in RNA polymerase bonding. Another sequence with a length of approximately 9 base pairs is located approximately 70 to 90 base pairs above the transcription starting point. This sequence is called the CAAT box and it is assumed that it plays a part in regulating the transcription level. Other regions above the transcription starting point have been identified which influence the frequency of transcription initiation in eukaryons. These DNA regions, known as enhancers, influence the activity of promoters in their vicinity. However, by definition, these sequences are not promoters, because their position does not have to be fixed.

In order to be able to express a foreign gene in an organism, e.g. a plant, the coding sequence of this gene must be placed under the control of a promoter and introduced into the plant. For inserting the gene to be expressed in the plant genome, the foreign DNA is usually brought into the Ti-plasmide of *agrobacterium tumefaciens* and the latter is then used for transforming the plants. A second, frequently used method is the direct transformation of DNA, e.g. with the aid of the "particle gun". Up to now, in most cases for this purpose use has been made of promoters isolated from bacteria or promoters of plant viruses, which lead to the expression of the foreign gene in the plants. For certain applications these promoters suffer from the disadvantage that they are of a different species and are consequently not subject to the control mechanisms within the plants.

When using a plant promoter it is possible to express a foreign gene, which is consequently also subject to the plant control mechanisms. By testing the expression of the gene in front of which the promoter was originally located, precise information can be obtained regarding the expression intensity, the time at which the gene is expressed and the expression location and these can be largely transferred to the expression of a foreign gene, placed under the control of this promoter. Another advantage is that when using a precisely characterized, plant promoter, planned interventions and research on the development of certain plant parts are possible.

Problem and Solution

The problem of the present invention is to make available a promoter, which is suitable for controlling the expression of nucleic acids in plants or plant cells. A partial aspect of the problem is to make available promoters having a high expression and simultaneously tissue specificity. In another aspect, the problem of the invention is to provide a process for the production of male, sterile plants.

One aspect of the problem of the invention is solved by a nucleic acid sequence coding for a promoter, which is both tapetum-specific and pollen-specific.

In a second aspect the problem is solved by a nucleic acid sequence coding for a promoter, the nucleic acid sequence covering a range of at least approximately 900 nucleotides upstream of the TATA box of the sequence represented in SEQ ID No. 1.

According to an embodiment, the nucleic acid sequence covers a range of at least approximately 1,000 nucleotides upstream of the TATA box of the sequence represented in SEQ ID No. 1.

According to another embodiment, the nucleic acid sequence covers a range of at least approximately 1,500 nucleotides upstream of the TATA box of the sequence represented in SEQ ID No. 1.

In yet another embodiment, the nucleic acid sequence covers the sequence represented in SEQ ID No. 1.

According to another aspect this problem is also solved by a nucleic acid sequence coding for a promoter, the nucleic acid sequence covering the sequence represented in SEQ ID No. 2.

In a fourth aspect the problem is solved by a nucleic acid sequence coding for a promoter, the nucleic acid sequence covering the sequence represented in SEQ ID No. 3.

In a fifth aspect the problem is solved by an expression system covering at least one of the nucleic acids according to the invention.

According to an embodiment, the expression system comprises at least one terminator and/or a linker.

In a sixth aspect the problem is solved by a nucleic acid construct comprising a nucleic acid sequence according to the invention and at least part of an expressible nucleic acid sequence.

According to an embodiment, the part of the expressible nucleic acid sequence or the complete, expressible sequence is linked with one of the nucleic acid sequences according to the invention in the sense direction.

In a preferred embodiment, the expressible nucleic acid codes for an invertase.

According to another preferred embodiment, the part of the nucleic acid sequence of an invertase or the complete sequence of an invertase is connected with one of the nucleic acid sequences according to the invention in the antisense direction.

According to an embodiment the invertase is of the type present in a structure selected from the group comprising anthers, tapetum, pollen precursor cells and pollen.

In another embodiment the invertase comes from the organism into which or into whose cells the nucleic acid construct is to be introduced and in particular from the plant group to which the species to be introduced into the nucleic acid construct belongs.

In yet another embodiment the organism is selected from the group comprising food plants, ornamental plants and medicinal plants.

In a seventh aspect the problem is solved by a vector comprising one of the nucleic acid sequences according to the invention and/or an expression system 9 according to the invention and/or a nucleic acid construct according to the invention.

In an eighth aspect the problem is solved by a cell, particularly a plant cell, comprising a nucleic acid according to the invention and/or an expression system according to the invention and/or a nucleic acid construct according to the invention and/or a vector according to the invention.

According to an embodiment the cell comprises a nucleic acid sequence according to the invention, which is a promoter, and a nucleic acid coding for an inhibitor of an invertase, the promoter controlling the expression of the inhibitor.

According to another embodiment the cell is selected from the group comprising pollen cells, pollen precursor cells and tapetum cells.

In a particularly preferred embodiment the cell is an arrested pollen cell.

In a ninth aspect the problem is solved by a plant incorporating a cell according to the invention.

According to an embodiment the plant is selected from the group comprising food plants, ornamental plants and medicinal plants, preferably chosen from the group comprising rice, maize, potatoes, tomatoes and rape.

In a further embodiment the plant is a male, sterile plant and has at least one further modification of its genotype, particularly a genetically engineering-caused change.

In a tenth aspect the problem is solved by a seed obtainable from a plant according to the invention.

In an eleventh aspect the problem is solved by a hybrid seed obtainable by hybridizing a male, sterile plant according to the invention with another male, fertile plant and the hybrid seed is obtained from the resulting filial generation.

In a twelfth aspect the problem is solved by a process for the production of male, sterile plants, a nucleic acid construct according to the invention being introduced into a cell, particularly into a plant cell and from said cell a plant is produced.

In an embodiment the plant is selected from the group comprising food, ornamental and medicinal plants, preferably selected from the group comprising rice, maize, potatoes, tomatoes and rape.

In a thirteenth aspect the problem is solved by the use of a nucleic acid construct according to the invention for producing male, sterile plants.

In a fourteenth aspect the problem is solved by the use of a nucleic acid sequence according to the invention for the expression of a nucleic acid sequence.

In a fifteenth aspect the problem is solved by a restorer plant, incorporating in a cell, preferably in most of its cells, a nucleic acid according to the invention as a promoter and a nucleic acid coding for a further invertase, which is controlled by said promoter, the further invertase being different from the cell's own invertase.

In a sixteenth aspect the problem is solved by a restorer plant, which can preferably be of the above-described type comprising in a cell and preferably in most of its cells, a nucleic acid according to the invention as a promoter and a nucleic acid coding for a saccharose transport system and which is controlled by said promoter.

According to an embodiment in a cell and preferably in most of its cells, it also incorporates a nucleic acid according to the invention as a promoter and a nucleic acid coding for saccharose synthase and/or and/or cytoplasmically expressed invertase, whose expression is controlled by the promoter.

In a seventeenth aspect the problem is solved by a plant, which is characterized in that in at least one cell and preferably in most of its cells it incorporates a nucleic acid construct according to the invention and the cell or cells also comprise a nucleic acid sequence according to the invention as a promoter and a nucleic acid coding for a further invertase and which is controlled by said promoter, the further invertase differing from the cell's own invertase.

In an eighteenth aspect the problem is solved by a plant, which is characterized in that in at least one cell and preferably in most of its cells, it incorporates a nucleic acid construct according to the invention and the cell or cells also comprise a nucleic acid sequence according to the invention as a promoter and a nucleic acid coding for a saccharose transport system and which is controlled by said promoter.

In a preferred embodiment the plant also comprises the features of the plant according to the seventeenth aspect of the present invention.

According to a further embodiment the plant comprises in at least one cell and preferably in most of its cells a nucleic acid construct according to the invention and the cell or cells also comprise a nucleic acid sequence according to the invention as a promoter and a nucleic acid coding for saccharose synthase and/or cytoplasmically expressed invertase, whose expression is controlled by the promoter.

In yet another embodiment the further invertase differing from the cell's own invertase is selected from the group of invertases incorporating invertase(s) of *Saccharomyces cerevisiae* and invertase(s) of *Zymomonas mobilis*.

According to another embodiment the saccharose synthase is of a heterologous or homologous origin.

In a further embodiment the cytoplasmically expressed invertase is of a homologous or heterologous origin.

In a particularly preferred embodiment the cytoplasmically expressed invertase is of heterologous origin and is preferably selected from the group of invertases including invertase(s) of *Saccharomyces cerevisiae* and invertase(s) of *Zymomonas mobilis*.

In a nineteenth aspect the problem is solved by a seed obtainable from a plant according to the invention.

In a twentieth aspect the problem is solved by the use of seed according to the invention for the in vitro embryogenesis of haploid or diploid or double diploid plants.

In a twenty first aspect the problem is solved by a fruit, particularly a seedless fruit obtainable from one of the plants according to the invention.

In a twenty second aspect the problem is solved by a fruit obtainable from one of the plants according to the invention and in particular from a restorer plant according to the invention and its hybridization products according to the invention.

In a twenty third aspect the problem is solved by a process for cloning promoters, which are functionally homologous to one of the promoters according to one of the preceding claims, the process being characterized by the following steps:
 a) cloning of anther-specific invertase cDNA by RT-PCR on mRNA from anthers, particularly using oligonucleotides OIN3 and OIN4,
 b) cloning the corresponding promoters.

The present invention is based on the surprising finding that promoters exist, which are suitable for the expression of nucleic acids in plant cells and have a double tissue specificity. The nucleic acids disclosed, which code for a promoter and which are referred to hereinafter as promoters for short, have an at least double specificity. They lead to the expression of the nucleic acid under their control in the tapetum and pollen. In addition, the promoters according to the invention are particularly strong and have a characteristic path over anther evolution subdivided into 12 phases and which makes it possible when using promoters according to the invention to obtain a time-defined, specific expression pattern. As a result of this both spatial specificity, i.e. tissue specificity, and time specificity such vectors offer a major advantage compared with promoters inducible by an exogenous stimulus, such as temperature or the presence of certain compounds. If such promoters are contained in the genome of a plant, there is a time and space-specific expression of the nucleic acid(s) under the control of said promoter.

The nucleic acid under the control of the promoter according to the invention can be any nucleic acid form. Correspondingly they can be coding nucleic acids or structural or functional nucleic acids.

The term coding nucleic acid is understood to mean more particularly a nucleic acid coding for a peptide or protein. The peptide/protein can e.g. be a structural protein or a peptide/protein having enzymatic activity.

A structural nucleic acid is more particularly understood to mean a nucleic acid leading to the formation of complexes, particularly with other molecules. It can inter alia be a rRNA and in particular an antisense nucleic acid.

A functional nucleic acid is more particularly understood to mean a nucleic acid, which exerts a specific action on a system, particularly a biological system. Such a specific action can e.g. be the aiding or inhibiting of translation or transcription. An example of a functional nucleic acid is an antisense nucleic acid.

It is clear to the expert that the above definitions relate to different aspects of nucleic acids and consequently do not represent exclusive definitions. It is in fact possible for the same nucleic acid to be covered by two or more of these definitions.

The promoters according to the invention permit the space and time-determined expression of nucleic acids, particularly of genes in plant cells and plants. These can be homologous or heterologous nucleic acids or genes. The homologous genes are those obtained from the genetic background of the plant containing one of the promoters according to the invention. Thus, the genes or nucleic acid sequences already present in the cell are either additionally or alternatively placed under the control of the promoters according to the invention. The heterologous genes or nucleic acids are those not coming from or present in the genetic background of the plant containing one of the promoters according to the invention.

The invention is also based on the surprising finding that it is possible to produce male, sterile plants, particularly when using one of the promoters according to the invention. For this purpose a nucleic acid coding for at least part of an invertase is placed under the control of one of the promoters according to the invention. The invertase is preferably of the type present in pollen and/or tapetum and which can come from the given plant species. Particular preference is given to the nucleic acid sequence according to SEQ ID No. 15 or part thereof. The invertase coded by SEQ ID No. 15 is of the type isolated from tobacco pollen. Part of the nucleic acid coding this invertase is brought under the control of the promoter according to the invention, so that the expression product of the nucleic acid coding the invertase acts as antisense nucleic acid and subsequently suppresses the expression of the invertase present in the pollen and tapetum. The antisense nucleic acid is produced in that the nucleic acid coding for the invertase or a part thereof is functionally coupled in the antisense direction to the promoter, optionally separated by an additional nucleic acid sequence, e.g. in the form of a linker. This is implemented in that the non-coding or antisense strand is read by the promoter and consequently the nucleic acid coding the invertase is incorporated in inverted form.

As will be shown hereinafter, under the influence of such a construct sterile pollen or sterile, male plants are formed. Without wishing to be bound by this, it would appear that as a result of the antisense nucleic acid the expression of the invertase in tapetum and in pollen is suppressed in that the antisense nucleic acid interacts with the sense nucleic acid, which is read by the gene of the invertase present in said tissues and consequently a translation no longer takes place. As a result the invertase titre in the tissues drops, so that firstly there is an energetic deficiency, particularly in the pollen and also the ratio of disaccharide, particularly saccharose, to one or both the monomers thereof changes. This leads to the observed infertility of the pollen and consequently the male infertility of plants carrying such pollen.

With respect to this mechanism it is significant that as a result of the tissue-specific and time expression pattern of the vectors according to the invention, the antisense nucleic acid specifically occurs if the invertase in said tissues is particularly active and must be suppressed in order to bring about the above-described, energetic deficiency and/or the shift of the disaccharide to monosaccharide ratio. As a result of the strength of the promoters according to the invention the antisense nucleic acid is expressed to such a significant extent that there is an effective suppression of the intrinsic invertase activity in pollen and tapetum. As a result of this sterile pollen and male, sterile plant formation mechanism, the pollen is arrested in a clearly defined stage of its development. This specific stage is referred to as the mononuclear microspore stage, which otherwise fertile pollen would pass through within the scope of normal development.

This mechanism for producing male sterility in plants not only occurs in tobacco or tomatoes. The promoter can in fact be used in any plant or plant species. The same applies in principle for nucleic acid coding for an invertase or part thereof functionally linked in antisense orientation with one of the promoters according to the invention. As, due to the mechanism, there is an interaction between the invertase intrinsically contained in the pollen (or the extracellular invertase produced by the same) or the nucleic acid coding it, particularly mRNA, it is advantageous in the corresponding constructs according to the invention to so select the invertase sequence used in the construct that it is identical with the sequence of the intrinsic invertase or has a degree of homology therewith allowing an interaction of the sense and antisense nucleic acid.

Another mechanism for producing male, sterile plants is co-suppression. The term co-suppression is understood to mean the effect that in the case of the overexpression of a gene already present in a plant, it does not lead to an increased formation of the peptide/protein coded by the gene and instead leads to a reduced formation. The action consequently corresponds to the antisense construct described herein comprising one of the promoters according to the invention and a nucleic acid, coding for an invertase and functionally coupled thereto in antisense orientation. Co-suppression evolves its action on the transcription plane. As a result the considerations made in connection with antisense construction concerning homologies of nucleic acid under one of the promoters according to the invention also apply here. Thus, this mechanism also represents a use possibility for the nucleic acid constructs disclosed herein, where a nucleic acid is bound in the sense orientation to one of the promoters according to the invention.

The usability of mechanisms according to the invention for the production of male sterility or for producing male, sterile plants is not restricted to specific plant families, types or species and it is instead a universally usable mechanism. Correspondingly plants are here understood to mean in general and in particular food, ornamental and medicinal plants. In the sense of the present invention, plants relate both to monocotyledons and dicotyledons, which present plant groups in the sense of the present invention. The use of invertases can extend both to invertases of or in both monocotyledons and dicotyledons. Despite the homology of invertases of monocotyledons and dicotyledons, there are distinct differences, which can be significant for construction or use. Another preferred group of plants, where different aspects of the invention can be applied or used, are rice maize, tomatoes, potatoes, rape, soya and sugar beet.

PREFERRED EMBODIMENTS

The claimed nucleic acid sequences coding for a promoter or promoter structure comprise the sequence according to SEQ. ID. No. 1, SEQ. ID. No. 2, SEQ. ID. No. 3 or in each case part thereof.

As described herein, the sequence of SEQ. ID. No. 1 was obtained from tobacco in a functionally oriented experiment and it was possible to show that the sequence as such has a promoter activity. The experts in the field are also aware of the fact that in such experiments frequently a longer sequence is obtained, which can have additions at the 5' or 3' end, which are unimportant for the promoter characteristics. In the present case the sequence according to SEQ. ID. No. 1 was further characterized and it was established that it was possible to shorten said sequence whilst maintaining the promoter characteristics. A shortening of the sequence of SEQ. ID. No. 1 to a sequence portion or range extending over approximately 900 nucleotides or base pairs/bp upstream, i.e. in the 5' direction from the so-called TATA box, provided adequate proof in the present case of the existence of promoter activity. Further embodiments of the promoter extend over a range of approximately 1000 or approximately 1500 nucleotides upstream of the TATA box.

The promoter according to SEQ. ID. No. 2 results from a promoter of SEQ. ID. No. 1, which is extended by approximately 1 kb compared with the latter.

The sequence according to SEQ. ID. No. 3 originally came from the tomato. In much the same way as the promoter based on the sequence according to SEQ. ID. No. 1, this promoter can be further shortened within the activity and knowledge of the expert or can be supplemented with additional elements, such as e.g. enhancers, whilst maintaining the promoter characteristics.

In the light of the finding forming the basis for the present invention, it is now possible to isolate corresponding, specific promoters from other species, i.e. promoters corresponding to the place and time-specific expression pattern of the promoters according to the invention and consequently functionally homologous thereto. In a first step anther-specific invertase cDNA is cloned by RT (reverse transcriptase) PCR on mRNA from anthers. In the following step the promoters controlling the same are cloned in a manner described in the present examples. Thus, the different applications of the promoters described here are not restricted to the promoters disclosed herein and characterized by their sequence, but instead extends to all those promoters having the presently described double tissue specificity.

Any random promoter according to the invention can be brought into an expression system and can be part of an expression system. The expression systems are preferably suitable for expression in plants. Expression systems, their components (such as linkers, terminators, insertion sequences, markers, etc.) and structure are described in the literature, such as e.g. Asubel, F. M.; Brent, R.; Kingston, R. E. et al (eds), 1999 Current protocols in molecular biology, John Wiley & Sons, Massachusetts; Sambrook, J.; Fritsch, E. F.; Maniatis, T.; 1989 Molecular Cloning: a laboratory manual. Cold Spring Harbor Laboratory, Cold Spring Harbor, N.Y.; Clark, M. S. (1997) Plant molecular biology—a laboratory manual, Spring, Berlin; Jones, H. (ed) Plant gene transfer and expression protocols, Methods in molecular biology, vol. 49, Humana Press Totowa; Weissbach A. and Weisbach H (eds), 1988 Methods for plant molecular biology, Academic Press, San Diego, whose disclosures are by reference incorporated into the present text.

Such expression systems can also be expression cassettes and there can in particular be restriction intersection points at a suitable distance from the promoter and other cassette parts, e.g. so-called linkers, which allow a cloning in of the nucleic acid sequence to be expressed. If the nucleic acid to be expressed is of the type coding for a peptide, polypeptide or protein, it must in particular be ensured that cloning in takes place in the reading range.

The expression systems according to the invention or the vectors containing them can be transformed with the aid of known procedures (see above literature) into plants or plant cells (e.g. *agrobacterium*-caused transformation; direct transformation, etc.).

The nucleic acid constructs according to the invention comprise at least one of the promoters according to the invention and at least part of an expressible nucleic acid sequence. As a function of the nature of the expressible nucleic acid sequence and the positioning thereof relative to the promoter, there are different application fields for said nucleic acid constructs.

As a result of the high expression strength of the promoter the latter is generally suitable for producing a high level of expression product. An expression product can be a mRNA, which is in turn translated into a peptide or protein. The translation product can in turn either have a direct action (in a biological system) or an indirect action. A direct action would e.g. be the production of a cytotoxin based on a peptide or the production of a structural protein. An indirect action would e.g. be the production of an enzyme catalyzing specific metabolic reactions, which in turn have an effect on the phenotype of the cell or the plant containing the same. However, another form of an expression product can be a functional nucleic acid. An example for this is constituted by the nucleic construct according to the invention and particularly that according to SEQ. ID. No. 8, which leads to the production of sterile pollen and consequently if such a construct is present in a plant, more specifically in its genome, leads to male, sterile plants.

If a particularly strong expression of the nucleic acid (sequence) to be expressed and which is under the control of one of the promoters according to the invention, it is typically functionally linked with the promoter in the sense direction or orientation. The sense or coding strand is that which is transcribed (unlike the antisense direction or orientation). An example of such a strong expressing nucleic acid construct is of the type described herein for co-suppression and its use for producing male, sterile plants. Another example of such a strong expressing nucleic acid construct consists of promoters according to the invention and nucleic acid or part thereof, which codes for an inhibitor of an invertase, particularly the invertase occurring in pollen and/or tapetum. The use of such a construct also represents a possibility of producing male sterility in plants. Moreover, as a result of this measure the construct according to the invention, where a promoter according to the invention is linked with a sequence coding for an invertase of part thereof and the sequence is connected functionally with the promoter in the antisense direction and which already leads to sterile pollen and therefore sterile plants, there can be a further reinforcement in its action of bringing about male sterility.

An inhibitor for an invertase is e.g. described by Rausch, T., Greiner, S., Krausgrill, S, 1998, Plant Physiol. 116, pp 733–742 and Krausgrill S. et al, 1998, plant J. 13, pp 275–280. In the case of the inhibitor cloned and described by Rausch et al it is a comparatively small protein of 17 kDa, which directly interacts with the invertase and blocks a complex and its enzymatic activity. In general, there are invertase inhibitors against extracellular and vacuolar invertases, all of which can be fundamentally used. Use is preferably made of an apoplasmic inhibitor, such as is described by Rausch et al. It is alternatively possible to use an intracellular invertase inhibitor, which is linked with an apoplasmic (extracellular space) targeting signal. In general terms, as a result of the strong expression, caused by the promoters according to the invention, of the nucleic acids under their control, which is both tissue-specific (pollen and tapetum-specific and therefore anther-specific) and also time-specific (only during pollen formation), large amounts of a specific protein, at a specific time, are produced by means thereof at a specific location (anthers) from transgenetic plants. The specific protein can be obtained in large quantities by harvesting the anthers, decomposition and specific purification processes for said protein.

Moreover, the promoters according to the invention and their use in transgenetic plants allow intervention in the development of the anthers of plants. An example is the already explained antisense expression of invertase sequences, as a consequence of which the quantity of extracellular invertase in the tapetum and pollen is reduced leading to male, sterile plants, which are important in agriculture in the production of hybrid seed.

Hybride seed is of fundamental importance for modern agriculture, because it gives particularly productive or high yield plants. Hybrid seed results from two genetically different parent parts, the difference in the genetic background being responsible for the special characteristics or the intensification of the positive characteristics in the filial generation compared with the parent plants. This is called the heterosis effect.

When cultivating plants for producing such hybrid plants it must consequently be ensured that there is no propagation of plants with the same genetic background. In the case of separate sex plants this can be ensured by spatial separation, but this does not provide the necessary reliability in every case. Alternatively the anthers of the male plants are manually removed, which is very time consuming and particularly in the case of small-flower plants and hybrids very difficult. The production of male, sterile plants and therefore the use of the promoters according to the invention and constructs containing them is consequently the method of choice here.

Further advantages result from the use of male, sterile plants. Thus, as a result of the limited nature of the invention leading to make sterility as a result of the use of the promoters according to the invention and the constructs containing them, the vegetative growth of the plant is not disturbed.

The advantages of the promoters according to the invention, the constructs containing them and the plants described hereinbefore in connection with the production of hybrid seed also apply to transgenetic plants, which can be given specific characteristics using genetic engineering methods (additionally for the introduction of one of the promoters according to the invention). In addition, when using male, sterile plants there is no risk of hybridizing out genetic changes to plants (due to the avoidance of flying pollen) growing wild or in neighbouring fields. Moreover, due to the specific nature of the intervention, i.e. the production of male sterility according to the invention, no interactions are to be expected with the additionally introduced, genetic changes. To this extent the promoters according to the invention and the constructs containing them represent particularly advantageous biological safety systems or transgenetic plants carrying in them said male sterility mechanisms, are particularly safe in the sense of excluding an undesired spread of plants modified by genetic engineering.

The promoters according to the invention and the constructs containing them can also be used for producing transgenetic plants, which produce plant's own substances in large quantities and which can act positively on the development of plants, particularly the yield of fruit-carrying plants. Examples of such plan's own substances are growth hormones or protein necessary for the energy supply of the growing tissue (e.g. invertases, sugar transporters). Such an increase can be directly caused by an introduced gene or result directly from an intervention in a control cycle. Examples of growth hormones having a preponderantly stimulating action are auxins, cytokinins, giberellins, brassinosteroids and jasmonate, whilst abscisinic acid and ethylene can be looked upon as preponderantly inhibiting growth hormones.

It is clear to the expert on the basis of his knowledge and also when taking account of the particular system to be modified, that the promoters according to the invention can be used not only for the up-regulation of production of compounds produced by the plant, but also for the reduction of substances produced by the plant, i.e. the plant's own substances (e.g. plant hormones). This reduction can be achieved by introducing degrading enzymes, inhibitors or so-called single-chain antibodies. Such systems can also be used for reducing male sterility, so that a combination of said system with the systems disclosed herein for producing male sterility can take place and consequently the extent of male sterility can be increased.

In the process according to the invention for producing male, sterile plants, introduction takes place into a plant cell of the presently disclosed nucleic acid construct according to SEQ. ID. No. 8 comprising one of the promoters according to the invention and functionally connected thereto a nucleic acid sequence coding for an invertase. The plant cell can be a random plant cell, particularly a leaf cell as a result of its totipotent character, i.e. its capacity to differentiate itself with each plant cell type. The plant cell provided with the construct is then developed or regenerated to a complete plant. This plant can then be vegetatively propagated, e.g. by slip propagation. A very similar procedure is used if male, sterile plants are produced using the nucleic acid construct or the system used for co-suppression.

A special form of plants according to the invention are so-called restorer plants. Such restorer plants are necessary for increasing the yield of sterile, fruit-carrying plants, such as e.g. maize and rape and for propagating male, sterile plants according to the invention.

These restorer plants are characterized in that they contain a construct leading to the production of an invertase. This invertase ensures the carbohydrate supply of the anthers and therefore tapetum and pollen. The invertase is preferably a heterologous invertase of the restorer plant, i.e. it differs from the invertase or invertases contained in the anthers, more precisely the tapetum and/or pollen. This invertase can also be different from that of the plant with which the restorer plant is to be hybridized. Suitable invertases are e.g. species-foreign invertases (e.g. invertases of *Saccaromyces cerevisiae* or bacteria such as *Zymomonas mobilis*). Instead of invertases it is also possible to use saccharose transport systems (for the transport of the saccharose over the cell membrane) in conjunction with intracellular saccharose-cleaving enzymes (e.g. saccharose synthase or neutral or vacuolar invertases). It is vital in the restorer plants according to the invention that the above-described, enzymatic activity restoring the sugar supply of the anthers is under the control of a promoter according to the invention.

If such restorer plants according to the invention are hybridized with the male, sterile plants according to the invention, both constructs in each case containing one of the promoters according to the invention are contained in a cell or a plant. As a result of the male sterility-causing nucleic acid construct according to the invention, an antisense nucleic acid is formed, which prevents the expression of the cell's own invertase and consequently interrupts the anther sugar supply, so that the pollen is sterile and consequently there is a drastic reduction to pollen production. However, simultaneously the construct introduced by the restorer plant into the plant (filial generation 1), and which comprises one of the promoters according to the invention and a nucleic acid for a preferably heterologous invertase or an above-described substitute system for the same, maintains a sugar supply. Due to the fact that for both constructs the same promoter or at least a similar promoter with respect to the expression behaviour is used, there is a compensation of the interruption of the sugar supply (as a result of the mechanism causing male sterility) through the restorer plant system ensuring the sugar supply. This is possible in that as a result of the difference in the invertase system of the restorer plant, the latter is not influenced and consequently impaired by the antisense mechanism of the male, sterile plant.

The restorer plants of the present invention can be subdivided into the three following groups. The first group comprises plants containing in their cells, preferably in most of their cells, one of the promoters according to the invention and a nucleic acid coding for a further invertase and which is controlled by said promoter, the further invertase differing from the cell's own or anther's own or plant's own invertase. The second group comprises plants containing in their cells and preferably most of their cells one of the promoters according to the invention and a nucleic acid coding for a saccharose transport system, said nucleic acid being controlled by said promoter. A subgroup of this second group of plants comprises yet a further of the promoters according to the invention and which controls an additionally present nucleic acid, which codes for a saccharose synthase and/or cytoplasmically expressed invertase. The third group of plants are restorer plants combining within them the constructs of the two first groups.

If the male, sterile plants of the present invention are hybridized with the restorer plants according to the invention, the different genotypes of the parent cells are combined and there is consequently a coexistence of the different nucleic acids coding for invertase activity or corresponding substitutes, in each case preferably under the control of one of the promoters according to the invention. The thus obtained plants according to the invention (filial generation 1) are male and fertile and supply hybrid seed, which is necessary for a further occurrence of the heterosis effect and the production of plants, in which the actual crop product is the seed, such as e.g. in the case of maize or rape.

Apart from the use of such restorer systems, it is also possible to make fertile again the male, sterile plant according to the invention and therefore convert it into a state allowing a sexual propagation, by evolving the pollen according to the invention arrested in the mononuclear microspore stage in an in vitro culturing to fertile pollen, which is then used for fertilizing plants, preferably transgenetic plants, the plants described therein and carrying therein one of the promoters according to the invention can also be called transgenetic plants.

The sterile pollen according to the invention of the male, sterile plants is present in arrested form in the mononuclear microspore stage. This pollen can now be used in order to obtain therefrom during in vitro embryogenesis haploid plants, which can in turn be cultivated inter alia to homozygotic, diploid plants. Thus, a system and process are made available providing homozygotic, diploid plants advantageous for plant growing purposes. This system is essentially made possible in that in the process according to the invention for the production of male, sterile plants or from the latter pollen can be produced, unlike in other processes for the production of male, sterile plants, where no pollen is formed, such as is e.g. the case in the cytotoxic process for the production of male, sterile plants (described in Mariani C. et al, 1990, Induction of male sterility in plants by a chimeric ribonuclease gene, Nature 347, pp 737–741.

The production of seedless fruit represents a further use of the male, sterile plants according to the invention.

A process for the production of haploid or dihaploid, homozygotic plants as an important starting material for plant cultivation consequently comprises the steps of obtaining the sterile pollen of a plant according to the invention and then regenerating it by in vitro embryogenesis to haploid or dihaploid plants. In vitro embryogenesis as such is known to the experts in the field and is e.g. described in Reynolds T. L. 1997, Pollen embryogenesis, Plant Mol. Biology 33, pp 1–10. Fundamentally a hunger and stress step is required for inducing in vitro embryogenesis. In the case of the male, sterile plants according to the invention the sugar supply is disturbed. Without wishing to be bound by this, it would appear that the pollen of the plants according to the invention has a higher competence to pass through in vitro embryogenesis and at least such pollen requires no further hunger or stress treatment. Thus, embryogenesis based on such pollen takes place more rapidly and efficiently.

DRAWINGS AND EXAMPLES

The invention is described in greater detail hereinafter relative to examples, which reveal further features, embodiments and advantages of the invention, together with the attached drawings.

BRIEF DESCRIPTION OF DRAWINGS

FIGS. 1A–1C Part (A), photographically the different stages of flower development in tobacco, part (B) the weight and length of tobacco anthers as a function of the flower development stages and part (C) invertase activity in wild pollen or sterile pollen.

FIG. 5 The sequence according to SEQ. ID. No. 1 supplemented by approximately 1 kb and the 5' end and carrying notations and referred to here as SEQ. ID. No. 2.

FIGS. 6A–6C In part (A), a photograph of an anther of a wt plant (top) and anthers of transgenetic tobacco plants (bottom), in which a beta-glucuronidase activity is under the control of one of the promoters according to the invention, in part (B) pollen of anther of transgenetic tobacco plants in which a beta-glucuronidase activity is under the control of one of the promoters according to the invention, in part (C), compared with (B), pollen of anthers of wild plants (wt).

FIG. 7 Raster electron micrographs and transmission-electron micrographs of wild tobacco plant pollen and a male, sterile plant according to the invention.

FIG. 10 Photographs of pollen of wild tobacco plants and male, sterile plants according to the invention.

FIG. 12 Photographs of anthers of transgenetic tomatoes containing a promoter according to the invention obtained from tobacco and controlling the expression of beta-glucuronidase.

FIG. 15 The genomic sequence of NIN 88.

FIG. 16 The construct according to the invention from the promoter according to SEQ. ID. No. 1 and the part of invertase NIN 88 with antisense orientation and under the control thereof and as also represented in SEQ. ID. No. 8.

FIG. 17 The sequence of LIN 7 with notations.

EXAMPLE 1

Flower Development in Tobacco Plants

Figure 2:
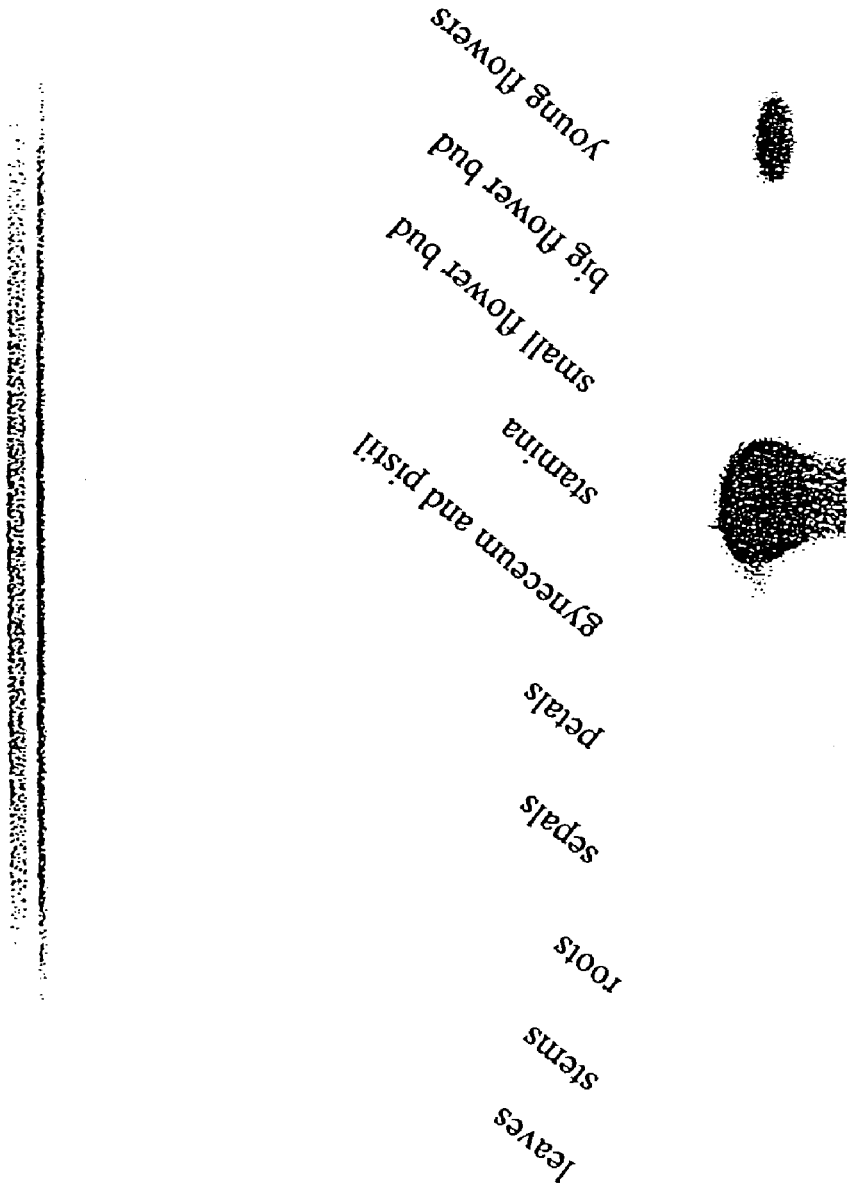
FIG. 2 An autoradiogram of a Northern Blot with which the localization of the extracellular invertase NIN 88 of tobacco is determined.

Flower or bloom development in tobacco plants is generally (Koltunow, A. M., 1990, Different temporal and spatial gene expression patterns occur during anther development, Plant Cell 2, pp 1201–1224), subdivided into a total of twelve different stages, shown in part (A) of FIG. 1. In the different stages there is a rapid increase in anther length up to stage 4, which then remains roughly constant in stages 4 to 10 and after a further rise in stag 11 drops back to the initial value in stage 12. With regards to the anther weight, there is also a rise up to stage 4, which continues less rapidly to stage 9, followed by a clear reduction in stages 9 to 11 and finally dropping in stage 12 to a value roughly below that in stage 1 (part (B) of FIG. 1). The enzymatic invertase activity in tobacco-pollen, expressed as $\mu$g glucose/miopollen*h, rises up to stage 9 and then drops again (FIG. 1, part (C)). Part (C) of FIG. 1 also shows the invertase activity of sterile pollen produced according to the present invention. The invertase activity is virtually constant independently of the development stage and consequently proves the successful inhibition of the invertase produced by the pollen by means of the construct illustrated in example 4 and which is represented in FIG. 16 and in SEQ. ID. No. 8.

EXAMPLE 2

Cloning of the Gene of Extracellular Invertase NIN 88 from Tobacco 750 bp cDNA fragment of extracellular invertase NIN 77 was cloned using reverse transcriptase of mRNA from tobacco anthers and PCR using oligonucleotides OIN 3 and OIN 4, which are primers developed for the cloning of plant invertases (Roitsch et al., 1995, Induction of apoplastic invertase of *Chenopodium rubrum* by D-glucose and a glucose analogue and tissue specific expression suggest a role in sink source regulation, Plant Physiol., 108, pp 285–294).

The sequence of OIN 3 is referred to herein as SEQ. ID. No. 4.

The sequence of OIN 4 is referred to herein as SEQ. ID. No. 5.

The thus found sequence of extracellular invertase NIN 77 or the cDNA fragment, is referred to herein as SEQ. ID. No. 6.

The cDNA fragment of NIN 77 was then used in order to screen a genomic bank of tobacco in phage lambda gt 10. The positive clones obtained were again screened using the oligonucleotide ONT 4. The sequence of ONT 4 is referred to herein as SEQ. ID. No. 7.

From a lambda clone were then subcloned two overlapping fragments in pUC19 vectors and then the clones were sequenced. Clone pNDG8.3 contains the complete promoter range and the 5' range of the structural gene, whereas clone pNDG8.1 contains the 3' range of the promoter and the complete structural gene. It was found that the cloned gene codes for an invertase differing from the extracellular invertase NIN 77. This novel, extracellular invertase was called NIN 88.

The genomic sequence of NIN 88 is shown in FIG. 15 and referred to as SEQ. ID. No. 15.

EXAMPLE 3

Expression Analysis of Extracellular Invertase NIN 88

Figure 3A:
FIGS. 3A–3C The special spatial and time pattern of the occurrence of NIN 88 protein, initially in the tapetum and then in the evolving pollen.
Figure 3B:
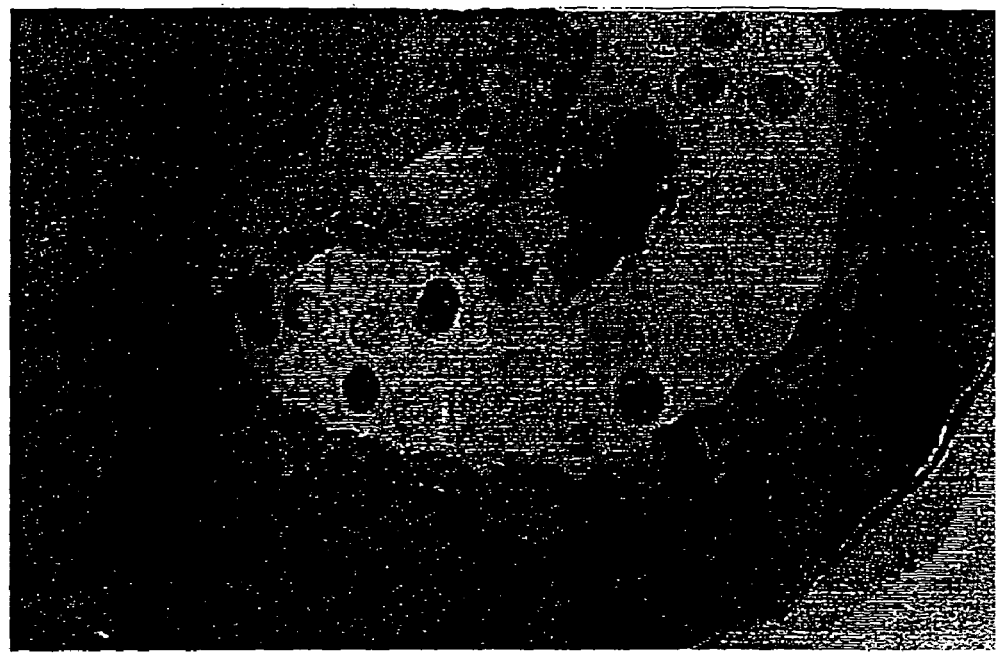
Figure 3C:

The expression analysis by Northern Blot shown in FIG. 2 reveals that mRNA is specifically localized in the anthers. To further specify the localization, an immunolocalization was performed in anther cross-sections using antibodies, directed against a fusion protein of NIN 88 and maltose binding protein. The result is shown in FIG. 3.

Extracellular invertase NIN 88 is initially localized in cells of the endothecium and tapetum and in a subsequent development stage in the evolving pollen, revealing a continuous activity rise of the extracellular invertase. The time sequence of the expression of NIN 88 is illustrated in parts A to C of FIG. 3. Part A of FIG. 3 shows the specific localization of NIN 88-protein in the tapetum in an anther cross-section. Identification takes place by immunolocalization, which reveals a dark border on the light, bean-shaped structure in the interior. During pollen evolution, NIN 88 can then be shown in tetrads (FIG. 3, part C) and subsequently in the pollen (FIG. 3, part B) in an anther cross-section using the above-described antiserum, detection for the tetrads being in the form of dark coloured, oval structures and for pollen in the form of round structures in the interior of the cut-into, light, bean-shaped structure.

This expression analysis made it possible to show that the promoter controlling the expression of extracellular invertase NIN 88 of tobacco is both tissue-specific (pollen and tapetum) and also evolution stage-specific.

EXAMPLE 4

Production of Nucleic Acid Constructs Comprising the Promoter of NIN 88

In the case of the NIN 88 gene cloning described in example 2, the promoter was also cloned as part of the gene, constituted by the promoter and other control elements, as well as the structural gene. Included in the description of example 2 was the designation of the plasmid (pNDG8.3) containing the promoter and the part of the NIN 88 gene used for the NIN 88 antisense construct.

The sequence shown in SEQ. ID. No. 1 is an approximately 3 kb fragment of the NIN 88 promoter. The sequence according to SEQ. ID. No. 1 is active as a promoter and comprises several pollen expression-specific, cis-active elements according to Madison et al, 1999, Plant. Mol. Biol., 41, pp 741–751:

| | |
|---|---|
| TGTGGTT | Twell et al., 1991 |
| GAARTTGTGA | Twell et al., 1991 |
| GAAA(NNNNNNN)TCCACCATA | Bate and Twell, 1998 |
| AAATGA | Weterings et al., 1995 |
| Long polyadenosine-rich regions in the 5'UTR | Bate et al., 1996 |

FIG. 5 shows the sequence according to SEQ. ID. No. 1, supplemented by approximately 1 kb at the 5' end and with the above notations. The additional 1 kb of SEQ. ID. No. 2 compared with SEQ. ID. No. 1 are located in front of the 5' end of SEQ. ID. No. 1.

The sequence according to SEQ. ID. No. 1 was fusioned as a promoter (referred to here as NIN 88 promoter) to various, differently coding sequences, as shown in FIG. 6.

The sequences were fusioned either in the sense orientation or in the antisense orientation. With sense orientation mRNA formation occurs and consequently there is a translation product, where as in antisense orientation antisense nucleic acid is formed, which interacts with sense nucleic acid and prevents the formation of a translation product. The following meanings are used for the different constructs:

| | |
|---|---|
| GUS | beta-glucuronidase |
| NIN 88 | extracellular invertase NIN 88 from tobacco |
| CIN 1 | extracellular invertase CIN1 from chenopodium rubrum EMBL Acc. No. X81792 |
| Ntβfruc1 | extracellular invertase Ntβfruc1 from tobacco EMBL Acc. No. X81834 |
| Invertase inhibitor | the apoplastic invertase inhibitor Nt-Inh1 from tobacco described by Rausch (Greiner S. et al. 1998, Cloning of a tobacco apoplasmic invertase inhibitor, Plant Physiol. 116, pp 733–742). |

EXAMPLE 4.1

Construct Promoter-GUS (Sense)

In this construct the approximately 3 kb fragment of SEQ. ID. No. 1 as a NIN 88 promoter was fusioned with the beta-glucuronidase gene as the reporter gene in a derivative of the plant transformation vector pBI101 in sense orientation and used for the transformation of tobacco (*Nicotiana tabacum* cv (=cultivar, variety. Xanthi und Samsun N N). The cloning strategy is described in example 4.3. The expression of the promoter in anthers was identified by histochemical identification of the beta-glucuronidase enzyme activity on tissues of intact anthers using the substrate X-GLUC. Identification of the expression of the promoter in pollen was provided both by histochemical identification of the beta-glucuronidase enzyme activity and by fluorometric identification in crude extracts using the substrate MUG.

The results of the histochemical identifications are shown in FIG. 6.

Part A of FIG. 6 shows the good histochemically stainable anthers as a result of the expression of beta-glucuronidase. Part B shows that, under the influence of the NIN 88 promoter, the beta-glucuronidase can also be identified in the pollen. The pollen of wt plants, i.e. wild plants, shown in part C is not stained.

EXAMPLE 4.2

Use of the Construct Promoter-GUS (sense) for the Transformation of Tomato and *Arabidopsis Thaliana*

Figure 11:
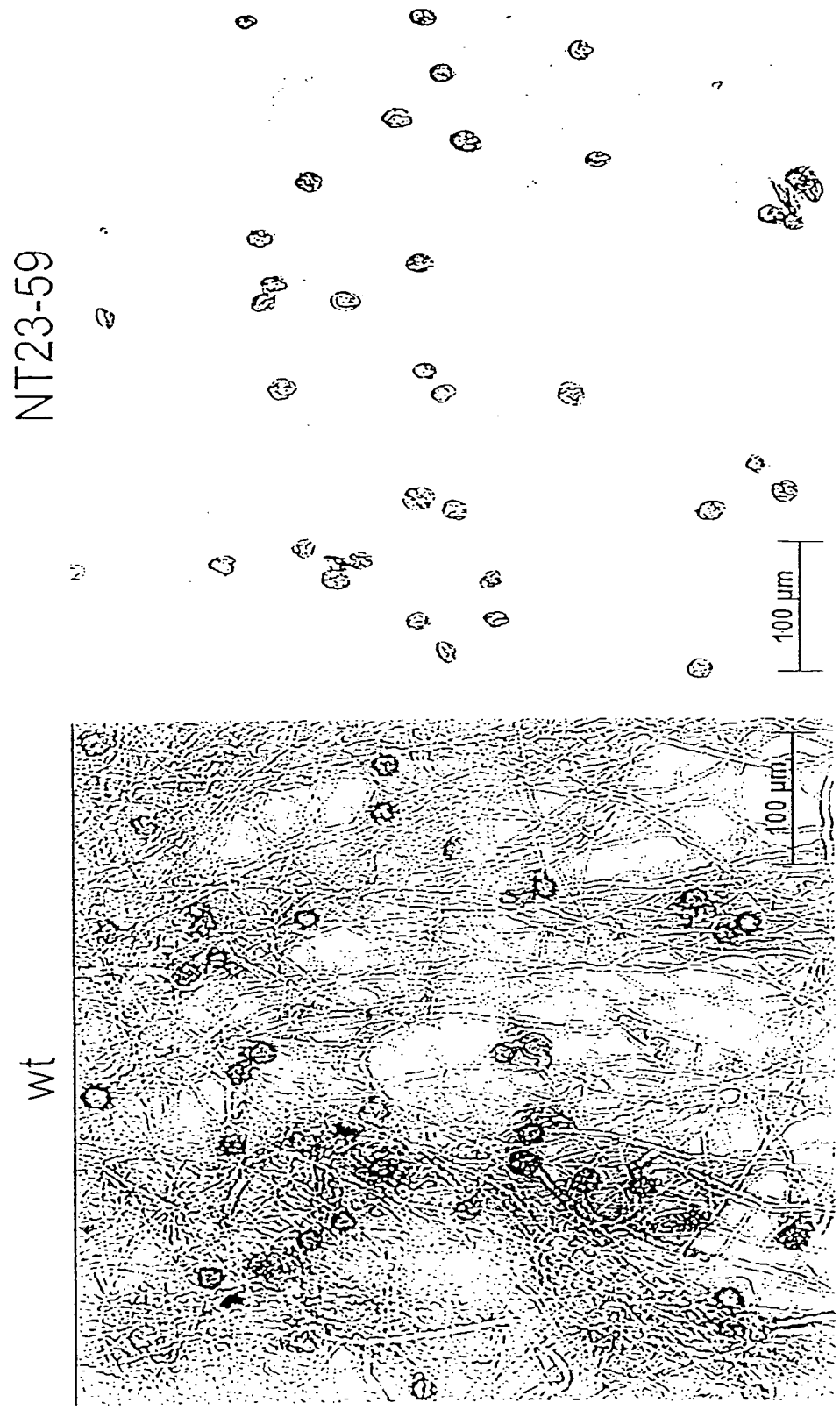
FIG. 11 Photographs of the germination of pollen of wild tobacco plants and male, sterile plants according to the invention.

The construct promoter GUS (sense) described in example 4.1 was also used for the transformation of tomatoes (*Lycopersicon peruvianum*). Once again the identification of the specific expression of the promoter in anthers and pollen was provided by the histochemical identification of the beta-glucuronidase enzyme activity. FIG. 11 shows that GUS activity is specifically detectable in the anthers of the transformed line LP1-8, but not in the anthers of a wt plant. Only in the case of the transformed tomato (LP 1-8), but not in the wild type, it is possible to histochemically stain the pollen as a result of the presence of beta-glucuronidase activity.

This construct was also used for transforming *Arabidopsis thaliana*. As in the case of *Lyopersicon*, a tissue and development stage-specific expression pattern of the reporter gene was established under the influence of the NIN 88 promoter.

It results from these transformation experiments that the promoters according to the invention and the constructs using them are not restricted to a particular plant variety or species with regards to their use and in fact they can be used universally for any plant.

EXAMPLE 4.3

Construct Promoter NIN 88 (Antisense)

As in the case of example 4.1, the NIN 88 promoter was used and on it was fusioned in the antisense orientation the sequence for the fragment of NIN 88 (corresponds to SEQ. ID. No. 6). This construct is referred to herein as SEQ. ID. No. 8 and is shown in FIG. 16.

EXAMPLE 4.3.1

The construction of the construct according to SEQ. ID. No. 8 takes place accompanied by the interposing of the construct described in example 4.1 promoter—beta-glucuronidase in the following way:
1. Cloning an approximately 3 kb fragment of NIN 88 promoter in the plant expression vector pBI101:
   Isolation of an approximately 3 kb XhoI-BamHI fragment of NIN 88 promoter from plasmid pNDG8.3.
   Linearization of plasmid pBI101 with salI and BamHI as the 5' end of the promoterless beta-glucuronidase gene.
   Ligating the fragment in the linearized vector and transformation into *E. coli* for construction of plasmid pNPG1.
2. Introduction of further restriction enzyme locations at the 3' end of the β-glucuronidase gene:
   Linearizing plasmid pNPG1 with SacI at the 3' end of the promoterless β-glucuronidase gene in front of the Nos terminator.
   Introduction of a linker sequence with the restriction enzyme points SacI-XhoI-HpaI-NdeI-SacI by means of the oligonucleotide NPVC1 (herein SEQ. ID. No. 9) and NPVC3 (herein SEQ. ID. No. 10) by hybridizing.
   Transformation into *E. coli* for construction of plasmid pNPG2.
3. Introduction of the missing 300 bp at the 3' end of the NIN 88 promoter and fusion of the 5' end of the coding sequence of NIN 88, more precisely the first 12 nucleotides, corresponding to 4 amino acids of the coding sequence including the start ATG (methionine) of NIN 88 with the coding sequence of the β-glucuronidase gene:
   Amplification of an approximately 300 bp fragment from the NIN 88 gene by PCR on pNDG8.3 with the primers NPK1 (herein SEQ. ID. No. 11) and NPK10 (herein SEQ. ID. No. 12) (in each case with the BamHI intersection point), restriction enzyme digestion with BamHI.
   Linearizing the plasmid pNPG2 with BamHI at the 5' end of the promoterless β-glucuronidase gene.
   Ligation of the fragment in the linearized vector and transformation to *E. coli* for construction of plasmid pNPG3 (NIN 88 promoter-GUS fusion).
4. Replacement of the glucuronidase gene by a NIN 88 cDNA sequence in antisense orientation:
   Amplification of an approximately 800 bp fragment, which is part of Exon III and therefore part of the cDNA of NIN 88 from the coding range of NIN 88 gene by PCR on pNDG8.3 with the primers NPK7 (herein SEQ. ID. No. 13) (with Xho intersection point) and NPK8 (herein SEQ. ID. No. 14), restriction enzyme digestion with XhoI.
   Cutting out the β-glucuronidase gene from plasmid pNPG3 by restriction enzyme digestion with SmaI and XhoI and isolation of the vector with the NIN 88 promoter and Nos terminator.
   Ligation of the fragment in the vector and transformation into *E. coli* for construction of plasmid pNPAN (NIN 88 promoter—NIN 88 antisense fusion).
   This construct can be used in order to produce the male, sterile plants of the present invention, in that it is transformed into a plant cell using known procedures and the obtained transformants are cultivated or regenerated to complete plants. The action mechanism occurring was described hereinbefore. The construct according to SEQ. ID. No. 8 was used for the transformation of tobacco (*Nicotiana tabacum* cv. Xanthi and Samsun NN).

EXAMPLE 4.3.2

The male, sterile plants obtained using the construct described in example 4.3.1 (invertase-antisense construct under the control of NIN 88 promoter), were then characterized.

The detection of the transformation was provided by PCR using primer NPK15 (specific for NIN 88 promoter), identified here as SEQ. ID. No. 16, and primer NPK19 (specific for NIN 88 antisense construct), identified here as SEQ. ID. No. 17.

Phenotypical characterization revealed the following:

There was a normal development of the plant overall and in particular the flowers and anthers. The plants, which revealed the strongest phenotype, are characterized by the following features:

Following the breaking open of the pollen sacs, far less pollen can be seen.

No normal seed capsules are formed.

Raster electron micrographs of the pollen of male, sterile plants reveal an abnormal form, as shown in FIG. 7 (wt stands for a wild type), NT 23-81 designates a male, sterile plant produced using the construct according to SEQ. ID. No. 8, as shown in FIG. 16.

Cross-sections in TEM show that the pollen is largely empty (FIG. 7).

Figure 8:
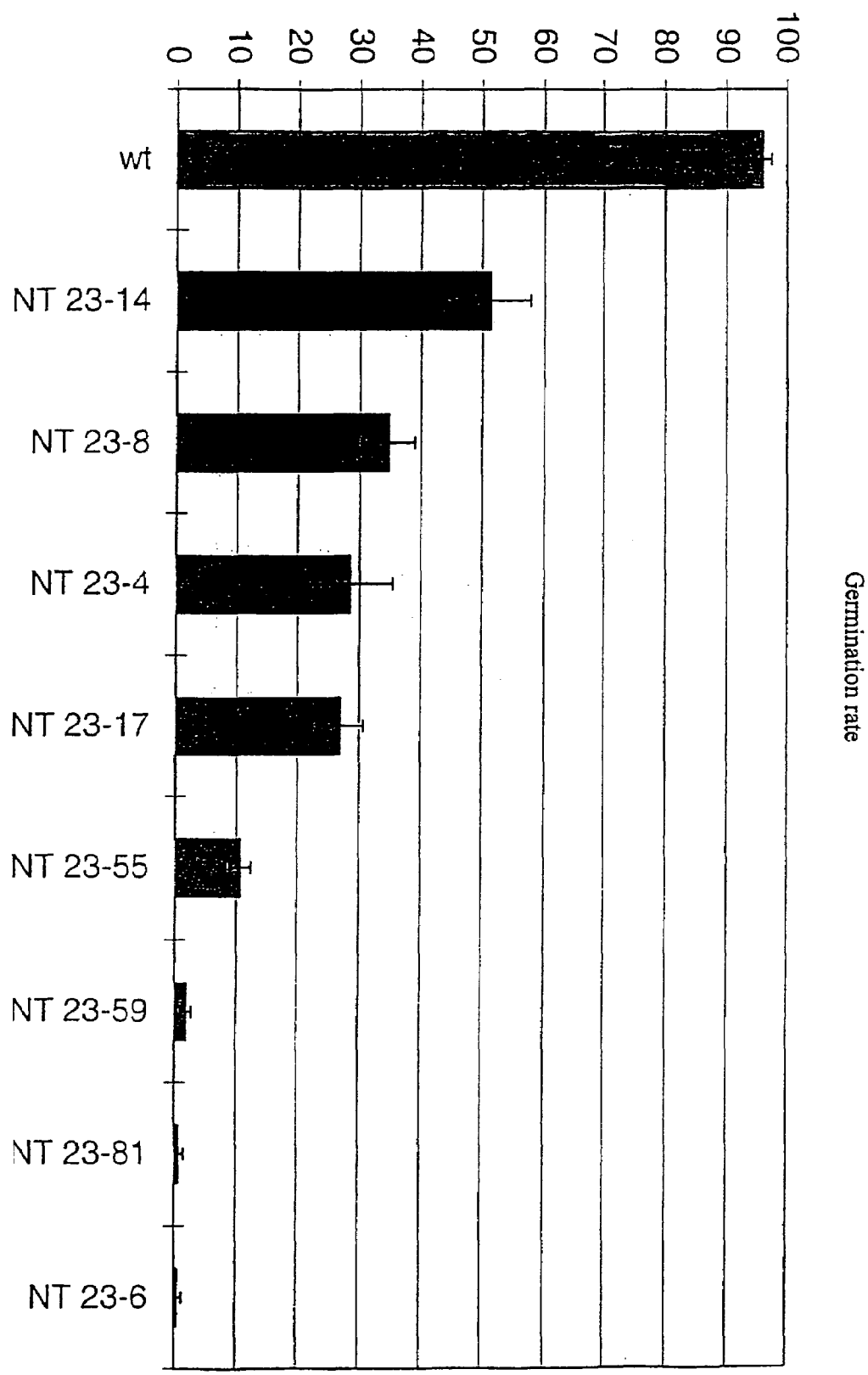
FIG. 8 A representation of the pollination of different forms of male, sterile plants according to the invention.

The germinatability of the pollen is less than 1%, cf. FIG. 8.

Figure 9:
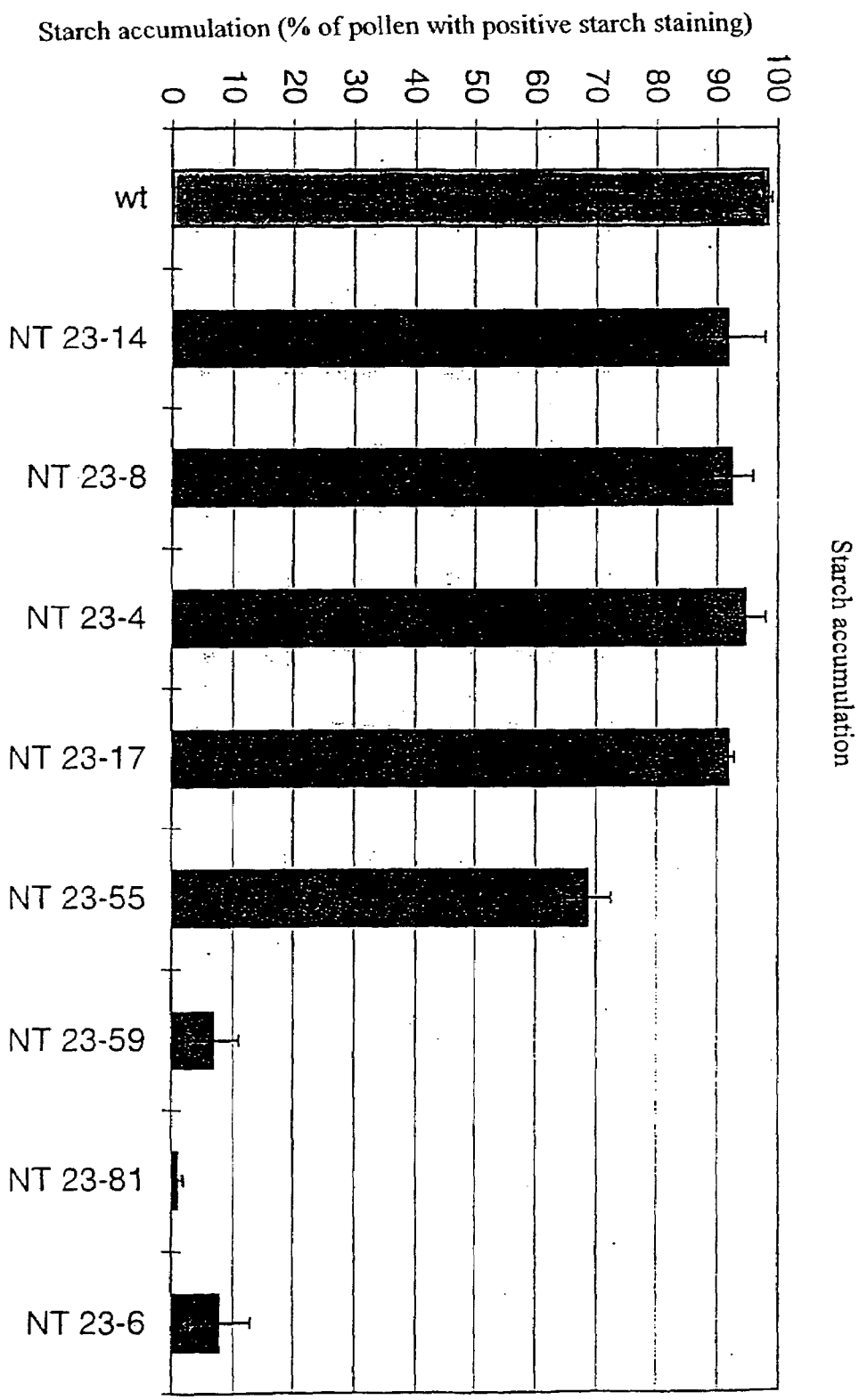
FIG. 9 A representation of the starch accumulation of different forms of male, sterile plants according to the invention.

The starch accumulation is lower, as is revealed by a negative starch staining (FIG. 9).

FIG. 10 shows light micrographs of pollen of the wild tobacco type and a male, sterile plant (NT 23-6) (produced using the construct of SEQ. ID. No. 8 and FIG. 16) supporting this finding and also showing that the sterile pollen is less developed.

Invertase activity in the anthers is normal.

Invertase activity in the pollen is significantly reduced and this confirms the weight specificity of the promoters according to the invention.

The pollen of the male, sterile plants according to the invention do not germinate (FIG. 11), but are still vital, as proved by staining with trypan blue and are arrested in a very early development stage, so that they are e.g. accessible to in vitro embryogenesis.

EXAMPLE 4.4

Further Constructs and Transformations Using NIN 88 Promoter

Figure 4:
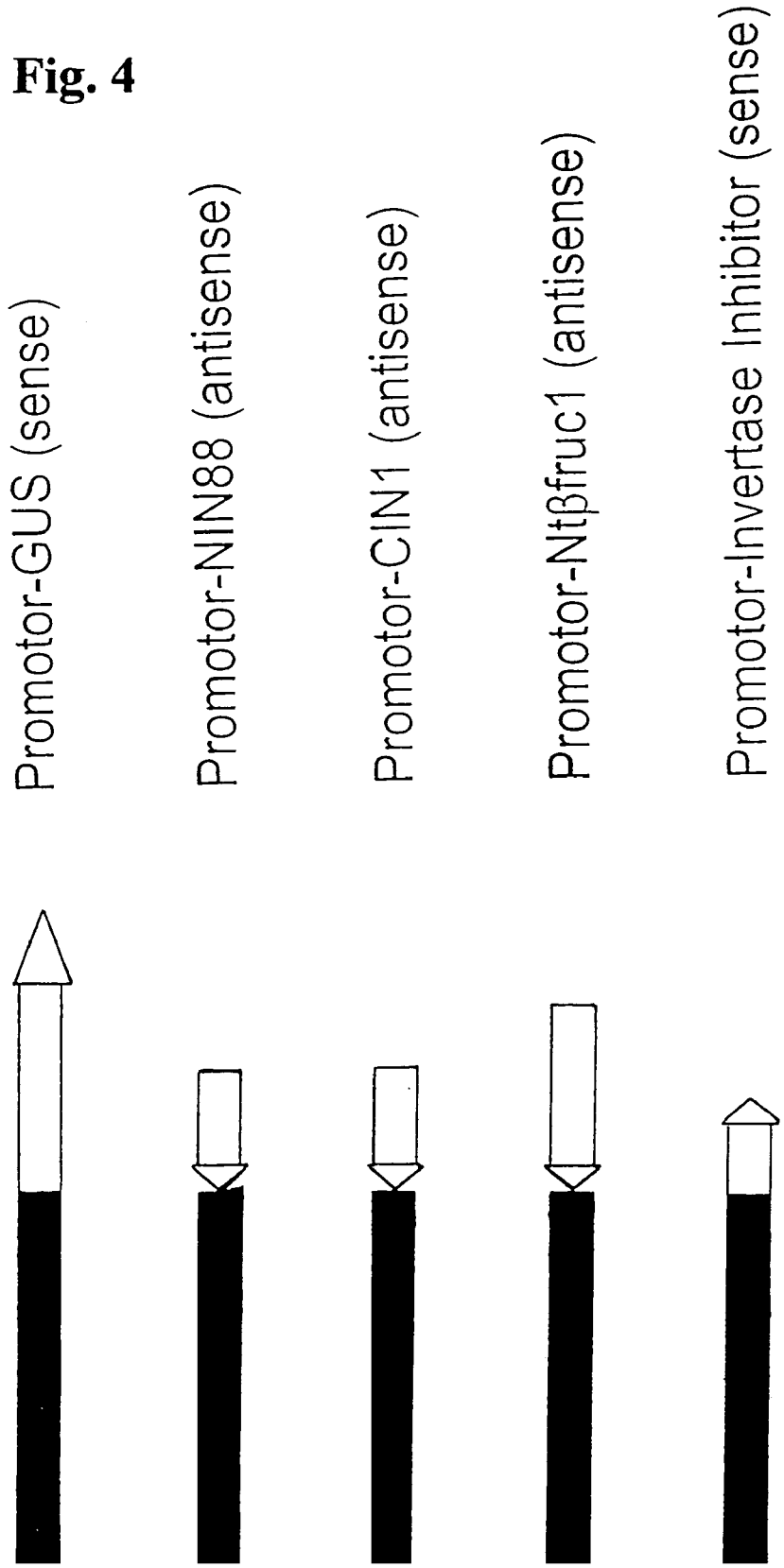
FIG. 4 A diagrammatic representation of different constructs comprising one of the promoters according to the invention.

Results of the lines obtained with other constructs, as shown in FIG. 4:

Detection of transformation:

Use was made of primers NPK15 (corresponding to SEQ. ID. No. 16—specific for NIN 88 promoter), NPK17 (corresponding to SEQ. ID. No. 18—CIN1 antisense), NPK18 (corresponding to SEQ. ID. No. 19—invertase inhibitor sense) and NPK20 (corresponding to SEQ. ID. No. 20—NTβfruc1-antisense).

Phenotype regarding the germinatability of pollen:

CIN1-antisense: reduction of germinatability of pollen by up to 98% NTβfruc1-antisense: reduction of germinatability of pollen by up to 91% Invertase-inhibitor sense: reduction of germinatability of pollen by up to 81%.

EXAMPLE 5

Pollen and Tapetum-Specific Promoter from Tomatoes

An approximately 750 bp fragment of extracellular invertase Lin7 from tomato was cloned by PCR with primers OIN3 and OIN4 of genomic DNA. Analysis of mRNA distribution revealed an anther-specific expression. Using the commercial genome Walk Kit (Strategen) and starting with the Lin7 partial sequence, a promoter with a comparable tissue and evolution stage specificity was also cloned from the tomato. The sequence of this promoter is referred to herein as SEQ. ID. No. 3.

Figure 13A:
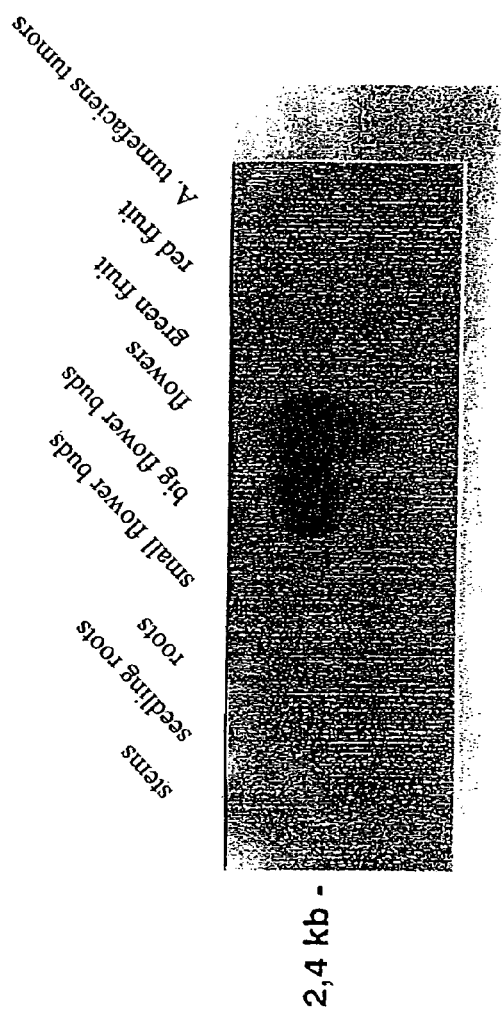
FIGS. 13A–13B A Northern Blot for detecting anther-specific expression of extracellular invertase LIN 7 in tomatoes.
Figure 13B:
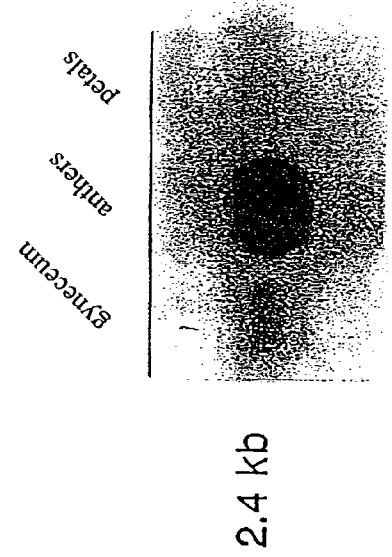
Figures 14A, 14B:
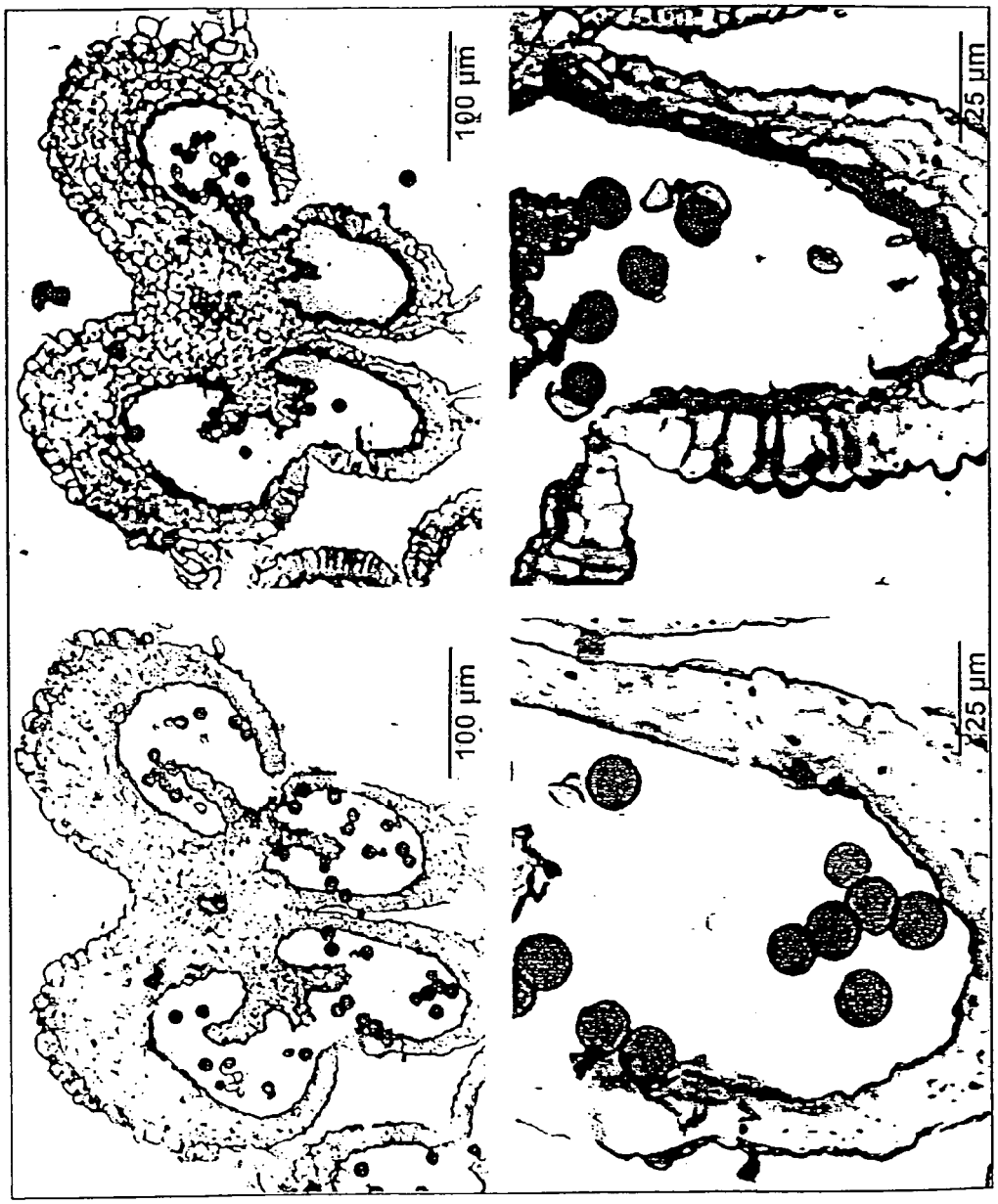
FIGS. 14A–14B The specific expression of LIN 7 in tapetum and pollen of tomatoes.

As can be gathered from FIG. 13, the extracellular invertase LIN 7 from the tomato under the control of the promoter according to SEQ. ID. No. 3 was also expressed in the pollen sacs of the tomato. The more precise localization of LIN 7, more specifically the distribution of mRNA of Lin 7, is shown in FIG. 14 and confirms the tissue specificity of the promoter of LIN 7, i.e. the promoter according to SEQ. ID. No. 3, expression taking place both in the tapetum and in the pollen. The designations "sense" and "antisense" in FIG. 14 here refer to a negative and positive control, because for the specific identification of a mRNA in tissue sections by in situ hybridization, use is made of a complimentary, hybridizing, single-strand, antisense RNA probe. A sense probe which cannot hybridize, because it has an identical base composition, is used as a negative control.

FIG. 17 shows the sequence of LIN 7 with notations and corresponding to SEQ. ID. No. 3.

A sequence analysis of LIN 7 revealed that this promoter carries a number of cis-acting elements, which are pollen-specific:

| | |
|---|---|
| TGTGGT | Twell et al., 1991 |
| GAAANNNNNNNTNNANNATN | Bate and Twell, 1998 |
| NANANTGTGA | Twell et al. 1991 |
| GTCAAAA | Zou et al. 1994 |
| Long polyadenosine-rich regions in the 5'-UTR | Bate et al. 1996 |

The CAAT box, TATA box and start codon ATG are in bold type.

The features of the invention disclosed in the above description, the drawings and the claims can be essential, both individually and in random combination, for the implementation of the different embodiments of the invention.

What is claimed is:

1. An isolated nucleic acid, comprising a tapetum-specific and a pollen-specific promoter, wherein the nucleic acid sequence comprises a range of at least 900 contiguous nucleotides upstream of the TATA box of the SEQ. ID. No. 1.

2. An isolated nucleic acid according to claim 1, wherein the nucleic acid sequence comprises a range of at least 1000 contiguous nucleotides upstream of the TATA box of the SEQ. ID. No. 1.

3. An isolated nucleic acid according to claim 1, wherein the nucleic acid sequence comprises a range of at least 1500 contiguous nucleotides upstream of the TATA box of the SEQ. ID. No. 1.

4. An isolated nucleic acid according to claim 1, wherein the nucleic acid sequence comprises the SEQ. ID. No. 1.

5. An isolated nucleic acid comprising a tapetum-specific and a pollen-specific promoter, wherein the nucleic acid sequence comprises the SEQ. ID. No. 2.

6. An expression system, comprising at least one isolated nucleic acid comprising a tapetum-specific and a pollen-specific promoter, wherein the nucleic acid sequence comprises a range of at least 900 contiguous nucleotides upstream of the TATA box of the SEQ. ID. No. 1.

7. The expression system according to claim 6, further comprising at least one terminator and/or a linker.

8. A nucleic acid construct, comprising a nucleic acid sequence according to claim 1 and at least part of a nucleic acid sequence selected from the group consisting of nucleic acid sequences which code for translation products, and functional nucleic acids.

9. The nucleic acid construct according to claim 8, wherein said part of the nucleic acid sequence or the complete sequence is connected in the sense direction with the nucleic acid sequence according to claim 1.

10. A vector comprising:
a nucleic acid sequence comprising a tapetum-specific and a pollen-specific promoter, wherein the nucleic acid sequence comprises a range of at least 900 contiguous nucleotides upstream of the TATA box of the SEQ. ID. No. 1 and/or
an expression system comprising at least one of said nucleic acid sequences, and/or
a nucleic acid construct comprising at least one of said nucleic acid sequences and at least part of a nucleic acid sequence selected from the group consisting of nucleic acid sequences which code for translation products, and functional nucleic acids.

11. A cell, comprising:
An isolated nucleic acid sequence comprising a tapetum-specific and a pollen-specific promoter, wherein the nucleic acid sequence comprises a range of at least 900 contiguous nucleotides upstream of the TATA box of the SEQ. ID. No. 1 and/or
an expression system comprising at least one of said nucleic acid sequences, and/or
a nucleic acid construct comprising at least one of said nucleic acid sequences and at least part of a nucleic acid sequence selected from the group consisting of nucleic acid sequences which code for translation products, and functional nucleic acids.

12. The cell according to claim 11, wherein the cell is selected from the group consisting of pollen cells, pollen precursor cells and tapetum cells.

13. The cell according to claim 11, wherein the cell is a pollen cell arrested in the mononuclear microspore stage.

14. A plant comprising a cell according to claim 11.

15. The plant according to claim 14, wherein the plant is selected from the group consisting of food plants, ornamental plants and medicinal plants.

16. The plant according to claim 14, wherein the plant is a male sterile plant and has at least one further modification of its genotype, wherein said modification is caused by genetic engineering.

17. A seed of the plant according to claim 14, wherein said seed comprises said isolated nucleic acid sequence.

18. A hybrid seed derived from crossing the male sterile plant according to claim 16 with another male fertile plant, wherein the hybrid seed is obtained from the resulting filial generation of said crossing, and wherein said seed comprises said isolated nucleic acid sequence.

19. A method for expression of a nucleic acid sequence, wherein said method comprises incorporating into a nucleic acid construct an isolated nucleic acid sequence comprising a tapetum-specific and a pollen-specific promoter, and wherein said nucleic acid sequence comprises a range of at least 900 contiguous nucleotides upstream of the TATA box of the SEQ ID NO:1.

20. A seedless fruit of a plant according to claim 14.

21. The plant according to claim 14, wherein the plant is selected from the group consisting of rice, maize, potatoes, tomatoes, rape, soya and sugar beet.

* * * * *

SEQUENCE LISTING

```
<160> NUMBER OF SEQ ID NOS: 13

<210> SEQ ID NO 1
<211> LENGTH: 1470
<212> TYPE: DNA
<213> ORGANISM: Unknown
<220> FEATURE:
<223> OTHER INFORMATION: Description of Unknown Organism:
      Clostridium-like vitulinus
<221> NAME/KEY: misc_feature
<222> LOCATION: (21)
<223> OTHER INFORMATION: n is unknown

<400> SEQUENCE: 1
gacgaacgct ggcggcgtgc ntaatacatg caagtagaac gctgaagact ttagcttgct      60
aaagttggaa gagttgcgaa cgggtgagta acgcgtaggt aacctgccta ctagcggggg     120
ataactattg gaaacgatag ctaataccgc ataacagcat ttaacacatg ttagatgctt     180 gaaggagca attgcttcac tagtagatgg acctgcgttg tattagctag ttggtgaggt     240
aacggctcac caaggcgacg atacatagcc gacctgagag ggtgatcggc cacactggga     300
ctgagacacg gcccagactc ctacgggagg cagcagtagg gaatcttcgg caatgggggc     360
aaccctgacc gagcaacgcc gcgtgagtga agaaggtttt cggatcgtaa agctctgttg     420
taagagaaga acgtgtgtga gagtggaaag ttcacacagt gacggtaact taccagaaag     480
```

-continued

```
ggacggctaa ctacgtgcca gcagccgcgg taatacgtag gtcccgagcg ttgtccggat        540
ttattgggcg taaagcgagc gcaggcggtt taataagtct gaagttaaag gcagtggctt        600
aaccattgtt cgctttggaa actgttagac ttgagtgcag aaggggagag tggaattcca        660
tgtgtagcgg tgaaatgcgt agatatatgg aggaacaccg gtggcgaaag cggctctctg        720
gtctgtaact gacgctgagg ctcgaaagcg tggggagcaa acaggattag ataccctggt        780
agtccacgcc gtaaacgatg agtgctaggt gttaggccct ttccggggct tagtgccgca        840
gctaacgcat taagcactcc gcctggggag tacgaccgca aggttgaaac tcaaaggaat        900 tgacggggc ccgcacaagc ggtggagcat gtggtttaat tcgaagcaac gcgaagaacc         960
ttaccaggtc ttgacatccc gatgctattc ctagagatag gaagtttctt cggaacatcg       1020
gtgacaggtg gtgcatggtt gtcgtcagct cgtgtcgtga tgttgggt taagtcccgc         1080 aacgagcgca acccctattg ttagttgcca tcattaagtt gggcactcta gcgagactgc       1140
cggtaataaa ccggaggaag gtggggatga cgtcaaatca tcatgcccct tatgacctgg       1200
gctacacacg tgctacaatg gttggtacaa cgagtcgcga gtcggtgacg gcaagcaaat       1260
ctcttaaagc caatctcagt tcggattgta ggctgcaact cgcctacatg aagtcggaat       1320
cgctagtaat cgcggatcag cacgccgcgg tgaatacgtt cccgggcctt gtacacaccg       1380
cccgtcacac cacgagagtt tgtaacaccc gaagtcggtg aggtaacctt ttggagccag       1440
ccgcctaagg tgggatagat gattggggtg                                         1470

<210> SEQ ID NO 2
<211> LENGTH: 666
<212> TYPE: DNA
<213> ORGANISM: Unknown
<220> FEATURE:
<223> OTHER INFORMATION: Description of Unknown Organism:
      Clostridium-like vitulinus

<400> SEQUENCE: 2
ccggatttat tgggcgtaaa gcgagcgcag gcggtttaat aagtctgaag ttaaaggcag         60
tggcttaacc attgttcgct ttggaaactg ttagacttga gtgcagaagg ggagagtgga       120
attccatgtg tagcggtgaa atgcgtagat atatggagga acaccggtgg cgaaagcggc       180
tctctggtct gtaactgacg ctgaggctcg aaagcgtggg gagcaaacag gattagatac       240
cctggtagtc cacgccgtaa acgatgagtg ctaggtgtta ggccctttcc ggggcttagt       300
gccgcagcta acgcattaag cactccgcct ggggagtacg accgcaaggt tgaaactcaa       360
aggaattgac ggggcccgc acaagcggtg gagcatgtgg tttaattcga agcaacgcga        420
agaaccttac caggtcttga catcccgatg ctatttctag ataggaag tttcttcgga        480 acatcggtga caggtggtgc atggttgtcg tcagctcgtg tcgtgagatg ttgggttaag       540
tcccgcaacg agcgcaaccc ctattgttag ttgccatcat taagttgggc actctagcga       600
gactgccggt aataaaccgg aggaaggtgg ggatgacgtc aaatcatcat gccccttatg       660
acctgg                                                                   666

<210> SEQ ID NO 3
<211> LENGTH: 662
<212> TYPE: DNA
<213> ORGANISM: Unknown
<220> FEATURE:
<223> OTHER INFORMATION: Description of Unknown Organism:
      Clostridium-like vitulinus
```

```
<400> SEQUENCE: 3
atttattggg cgtaaagcga gcgcaggcgg tttaataagt ctgaagttaa aggcagtggc      60
ttaaccattg ttcgctttgg aaactgttag acttgagtgc agaagggag agtggaattc     120 catgtgtagc ggtgaaatgc gtagatatat ggaggaacac cggtggcgaa agcggctctc    180
tggtctgtaa ctgacgctga ggctcgaaag cgtgggagc aaacaggatt agataccctg     240
gtagtccacg ccgtaaacga tgagtgctag gtgttaggcc ctttccgggg cttagtgccg    300
cagctaacgc attaagcact ccgcctgggg agtacgaccg caaggttgaa actcaaagga    360
attgacgggg gcccgcacaa gcggtggagc atgtggttta attcgaagca acgcgaagaa    420
ccttaccagg tcttgacatc ccgatgctat ttctagagat aggaagtttc ttcggaacat    480
cggtgacagg tggtgcatgg ttgtcgtcag ctcgtgtcgt gagatgttgg gttaagtccc    540
gcaacgagcg caaccccctat tgttagttgc catcattaag ttgggcactc tagcgagact    600
gccggtaata accggagga aggtggggat gacgtcaaat catcatgccc cttatgacct     660
gg                                                                   662

<210> SEQ ID NO 4
<211> LENGTH: 1451
<212> TYPE: DNA
<213> ORGANISM: Unknown
<220> FEATURE:
<223> OTHER INFORMATION: Description of Unknown Organism:
      Clostridium-like vitulinus

<400> SEQUENCE: 4
gatgaacgct ggcggcgtgc ctaatacatg caagtcgaac gggaatcttc ggattccagt      60
ggcgaacggg tgaggaatac ataggtaacc tgcccctccg aggggacaa cagacggaaa     120 catctgctaa gaccgcatag ccacagggaa ggcatcttcc ctgtgccaaa tgtcctttcg    180
gggacagcgg ggggatggac ctatgccgca ttagctggtt ggcggggcaa cggcccacca    240
aggcgacgat gcgtagccgg cctgagaggg cggacggcca cactgggact gagacacggc    300
ccagactcct acgggaggca gcagtaggga attttcggca atgggggaaa ccctgaccga    360
gcaacgccgc gtgaacgatg aaggccttcg ggtcgtaaag ttctgttgcg aaggaagaac    420
gccggtgtca ggaaatgggc gccgggtgac ggtacttcgc atagaaagcc acggctaact    480
acgtgccagc agccgcggta atacgtaggt ggcgagcgtt atccggaatc attgggcgta    540
aagagggagc aggcggcgat acaggtctgt ggtgaaattc cgaagctaaa cttcggccag    600
ccaaagaaac cggatcgcta gagtgcggaa gaggatcgtg gaattccatg tgtagcggtg    660
aaatgcgtag atatatggag gaacaccagt ggcgaaggcg acggtctggg ccgcaactga    720
cgctcattcc cgaaagcgtg gggagcaaat aggattagat accctagtag tccacgccgt    780
aaacgatcga tactaagtgt cgggggtcaa acctcggtgc tggagtcaac gcaataagta    840
tcgcgcctga gtagtacgtt cgcaagaatg aaactcaaag gaattgacgg gggcccgcac    900
aagcggtgga gcatgtggtt taattcgaag caacgcgaag aaccttacca ggtcttgaca    960
tcgatccaaa agggacggag acgtccccat agctatggag aagacaggtg gtgcatggtt   1020
gtcgtcagct cgtgtcgtga gatgttgggt taagtcccgc aacgagcgca accctgtcg    1080 ccagttgcca gcattgagtt ggggactctg gcgagactgc ctctgcaagg aggaggaagg   1140
cggggatgac gtcaaatcat catgcccctt atgacctggg ccacacacgt gctacaatgg   1200
acggagcaga gggaagcgaa gcggcgacgc caagcggatc ccagaaaccc gttctcagtt   1260
```

```
cggactgcag tctgcaactc gactgcacga agctggaatc gctagtaatc gcggatcagc      1320
atgccgcggt gaatacgttc tcgggccttg tacacaccgc ccgtcacacc atgagagtcg      1380
gcaacacccg aagccggtgg ctcaacccct cggggaggga gctgtctaag gtggggccga      1440
tgattggggt g                                                          1451

<210> SEQ ID NO 5
<211> LENGTH: 1451
<212> TYPE: DNA
<213> ORGANISM: Unknown
<220> FEATURE:
<223> OTHER INFORMATION: Description of Unknown Organism:
      Clostridium-like vitulinus

<400> SEQUENCE: 5
gatgaacgct ggcggcgtgc ctaatacatg caagtcgaac gggaatcttc ggattccagt        60
ggcgaacggg tgaggaatac ataggtaacc tgcccctccg aggggggacaa cagacggaaa      120 catctgctaa gaccgcatag ccacagggaa ggcatcttcc ctgtgccaaa tgtcctttcg      180
gggacagcgg ggggatggac ctatgccgca ttagctggtt ggcggggcaa cggcccacca      240
aggcgacgat gcgtagccgg cctgagaggg cggacggcca cactgggact gagacacggc      300
ccagactcct acgggaggca gcagtaggga attttcggca atgggggaaa ccctgaccga      360
gcaacgccgc gtgaacgatg aaggccttcg ggtcgtaaag ttctgttgcg aaggaagaac      420
gccggtgtca ggaaatgggc gccgggtgac ggtacttcgc atagaaagcc acggctaact      480
acgtgccagc agccgcggta atacgtaggt ggcgagcgtt atccggaatc attgggcgta      540
aagagggagc aggcggcgat acaggtctgt ggtgaaattc cgaagctaaa cttcggccag      600
ccaaagaaac cggatcgcta gagtgcgaaa gaggatcgtg gaattccatg tgtagcggtg      660
aaatgcgtag atatatggag gaacaccagt ggcgaaggcg acggtctggg ccgcaactga      720
cgctcattcc cgaaagcgtg gggagcaaat aggattagat accctagtag tccacgccgt      780
aaacgatcga tactaagtgt cgggggtcaa acctcggtgc tggagtcaac gcaataagta      840
tcgcgcctga gtagtacgtt cgcaagaatg aaactcaaag gaattgacgg gggcccgcac      900
aagcggtgga gcatgtggtt taattcgaag caacgcgaag aaccttacca ggtcttgaca      960
tcgatccaaa agggacggag acgtccccat agctatggag aagacaggtg gtgcatggtt     1020
gtcgtcagct cgtgtcgtga tgttgggt taagtcccgc aacgagcgca acccctgtcg      1080
ccagttgcca gcattgagtt ggggactctg gcgagactgc ctctgcaagg aggaggaagg     1140
cggggatgac gtcaaatcat catgcccctt atgacctggg ccacacacgt gctacaatgg     1200
acggagcaga gggaagcgaa gcggcgacgc aagcggatcc ccagaaaccc gttctcagtt     1260
cggactgcag tctgcaactc gactgcacga agctggaatc gctagtaatc gcggatcagc     1320
atgccgcggt gaatacgttc tcgggccttg tacacaccgc ccgtcacacc atgagagtcg     1380
gcaacacccg aagccggtgg ctcaacccct cggggaggga gctgtctaag gtggggccga     1440
tgattggggt g                                                         1451

<210> SEQ ID NO 6
<211> LENGTH: 1483
<212> TYPE: DNA
<213> ORGANISM: Unknown
<220> FEATURE:
<223> OTHER INFORMATION: Description of Unknown Organism:
      Clostridium-like vitulinus

<400> SEQUENCE: 6
```

```
gacgaacgct ggcggcgtgc ttaacacatg caagtcgaac gaggygatttt waagcttgct      60 tagatgagtc gagtggcaaa cgggtgagta acgcgtagac aacctgccgc aaagatgggg     120
acaacagtcc gaaaggactg ctaataccga atgttgtcag attcccgcat gggagactga     180
ttaaagatgg cctctacttg taagctatcg ctttgcgatg ggtctgcgtc tgattagcta     240
gttggtgggg taacggccta ccaaggcgac gatcagtagc cggtctgaga ggatgaacgg     300
ccacattgga actgagacac ggtccagact cctacgggag gcagcagtgg ggaatcttcc     360
gcaatgggcg aaagcctgac ggagcaacgc cgcgtgagtg aagaagggtt tcggctcgta     420
aagctctgtt gacggggacg aacgtgcgag atgcgaatag tttcttgcaa tgacggtacc     480
cgtcgaggaa gccacggcta actacgtgcc agcagccgcg gtaatacgta ggtggcgagc     540
gttgtccgga attattgggc gtaaagggag cgcaggcggg aaggcaagtc agtcttaaaa     600
gtgcggggct caaccccgtg atgggattga aactgtcttt cttgagtgca ggagaggaaa     660
gcggaattcc tagtgtagcg gtgaaatgcg tagatattag gaggaacacc agtggcgaag     720
gcggctttct ggactgtaac tgacgctgag gctcgaaagc gtggggagcg aacaggatta     780
gataccctgg tagtccacgc cgtaaacgat gaatgctagg tgtaggaggt atcgacccct     840
tctgtgccgg agttaacgca ataagcattc cgcctgggga gtacggtcgc aagactgaaa     900
ctcaaaggaa ttgacggggg cccgcacaag cggtggagta tgtggtttaa ttcgacgcaa     960
cgcgaagaac cttaccaggg cttgacattg agtgaaaggc ctagagattg gtccctctct    1020
tcggagacac gaaaacaggt ggtgcatggc tgtcgtcagc tcgtgtcgtg agatgttggg    1080
ttaagtcccg caacgagcgc aacccctatc atttgttgcc agcacgtcaa ggtgggaact    1140
caaatgagac tgccgcggac aacgcggagg aaggcgggga tgacgtcaag tcatcatgcc    1200
ccttatgtcc tgggctacac acgtactaca atgggatgga cagagagcag cgaccccgcg    1260
agggcaagcg aaccccataa accatctccc agttcggatt gcaggctgca acccgcctgc    1320
atgaagtcgg aatcgctagt aatcgctggt cagcatacag cggtgaatac gttcccgggc    1380
cttgtacaca ccgcccgtca caccacgaaa gtcattcaca cccgaagccg gtgggtaaac    1440
cgcaaggata tagccgtcta aggtgggggc gatgactggg gtg                     1483
```

<210> SEQ ID NO 7
<211> LENGTH: 1000
<212> TYPE: DNA
<213> ORGANISM: Unknown
<220> FEATURE:
<223> OTHER INFORMATION: Description of Unknown Organism:
      Clostridium-like vitulinus

<400> SEQUENCE: 7

```
cgaggaagcc acggctaact acgtgccagc agccgcggta atacgtaggt ggcgagcgtt      60
gtccggaatt attgggcgta aagggagcgc aggcggaag taagtcggt cttaaaagtg     120 cggggctcaa ccccgtgatg ggatcgaaac tatctttctt gagtgcagga gaggaaagcg     180
gaattcctag tgtagcggtg aaatgcgtag atattaggag gaacaccagt ggcgaaggcg     240
gctttctgga ctgtaactga cgctgaggct cgaaagcgtg gggagcgaac aggattagat     300
accctggtag tccacgccgt aaacgatgaa tgctaggtgt aggaggtatc gaccccttct     360
gtgccggagt taacgcaata agcattccgc ctggggagta cggtcgcaag actgaaactc     420
aaaggaattg acgggggccc gcacaagcgg tggagtatgt ggtttaattc gacgcaacgc     480
gaagaacctt accagggctt gacattgagt gaaagggcta gagatagctc cctctcttcg     540
```

```
gagacacgaa acacaggtggt gcatggctgt cgtcagctcg tgtcgtgaga tgttgggtta    600
agtcccgcaa cgagcgcaac ccctatcttt tgttgccagc acgtcacggt gggaactcaa    660
aagagactgc cgcggacaac gcggaggaag gcggggatga cgtcaagtca tcatgcccct    720
tatgtcctgg gctacacacg tactacaatg ggatggacag agagcagcga acccgcgagg    780
gcaagcgaac cccataaacc atctcccagt tcggattgca ggctgcaact cgcctgcatg    840
aagtcggaat cgctagtaat cgcaggtcag catactgcgg tgaatacgtt cccgggcctt    900
gtacacaccg cccgtcacac cacggaagtc attcacaccc aaagccggtg gggtaacctt    960
cgggagccag ccgtctaagg tgggggcgat gactggggtg                         1000
```

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: 27f primer

<400> SEQUENCE: 8
agagtttgat cctggctcag                                                 20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: 1492r
      primer

<400> SEQUENCE: 9
ggttaccttg ttacgact                                                   18

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: 530f primer

<400> SEQUENCE: 10
gtgccagcmg ccgcgg                                                     16

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: 519r primer

<400> SEQUENCE: 11
gwattaccgc ggckgctg                                                   18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: 907r primer

<400> SEQUENCE: 12
ccgtcaattc mtttragttt                                                 20
```

-continued

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: 926f primer

<400> SEQUENCE: 13
aaactyaaak gaattgacgg                                               20
```